US010308956B2

(12) United States Patent
Verstegen et al.

(10) Patent No.: US 10,308,956 B2
(45) Date of Patent: Jun. 4, 2019

(54) HVT-VECTORED ND-IBD VACCINE

(71) Applicant: Intervet Inc., Madison, NJ (US)

(72) Inventors: Iwan Verstegen, Boxmeer (NL); Paulus Jacobus Antonius Sondermeijer, Boxmeer (NL); Paul Vermeij, St. Anthonis (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/110,628

(22) PCT Filed: Dec. 23, 2015

(86) PCT No.: PCT/EP2015/081121
§ 371 (c)(1),
(2) Date: Jul. 8, 2016

(87) PCT Pub. No.: WO2016/102647
PCT Pub. Date: Jun. 30, 2016

(65) Prior Publication Data

US 2017/0306353 A1 Oct. 26, 2017

(30) Foreign Application Priority Data

Dec. 24, 2014 (EP) .................................... 14200340

(51) Int. Cl.

| | |
|---|---|
| ***C12N 15/86*** | (2006.01) |
| ***A61K 39/12*** | (2006.01) |
| ***A61K 39/17*** | (2006.01) |
| ***A61K 39/295*** | (2006.01) |
| ***C07K 14/005*** | (2006.01) |
| *A61K 39/00* | (2006.01) |

(52) U.S. Cl.
CPC .............. *C12N 15/86* (2013.01); *A61K 39/12* (2013.01); *A61K 39/17* (2013.01); *A61K 39/295* (2013.01); *C07K 14/005* (2013.01); *A61K 2039/5256* (2013.01); *A61K 2039/54* (2013.01); *A61K 2039/552* (2013.01); *A61K 2039/70* (2013.01); *C12N 2710/16343* (2013.01); *C12N 2720/10022* (2013.01); *C12N 2720/10034* (2013.01); *C12N 2720/10071* (2013.01); *C12N 2760/18134* (2013.01); *C12N 2760/18171* (2013.01); *C12N 2830/34* (2013.01); *C12N 2830/50* (2013.01); *C12N 2830/60* (2013.01)

(58) Field of Classification Search
CPC ...... A61K 39/12; A61K 39/295; A61K 39/17; C07K 14/005; C12N 15/86
See application file for complete search history.

(56) References Cited

U.S. PATENT DOCUMENTS

| | | | |
|---|---|---|---|
| 5,961,982 | A | 10/1999 | Cochran |
| 5,980,906 | A | 11/1999 | Audonnet et al. |
| 6,045,803 | A | 4/2000 | Audonnet et al. |
| 2014/0147457 | A1 | 5/2014 | Bublot et al. |

FOREIGN PATENT DOCUMENTS

| | | | |
|---|---|---|---|
| EP | 0431668 | B1 | 11/1990 |
| EP | 1026246 | A1 | 10/2000 |
| EP | 0719864 | B1 | 11/2003 |
| EP | 1298139 | B1 | 5/2007 |
| WO | WO198704663 | A1 | 7/1987 |
| WO | WO199325665 | A1 | 12/1993 |
| WO | WO199605291 | A1 | 2/1996 |
| WO | W02009156367 | A1 | 12/2009 |
| WO | W02013057235 | A1 | 4/2013 |
| WO | W02013057236 | A1 | 4/2013 |
| WO | 2013144355 | A1 | 10/2013 |
| WO | W02016087560 | A1 | 6/2016 |

OTHER PUBLICATIONS

Cronenberg, A.M. et al, Vaccination of broilers with HVT exressing an Eimeria acervulina antigen improves performance after challenge with Eimeria, Acta Virol., 1999, pp. 192-197, 43(2-3).
Dartiel, et al., Herpesvirus of Turkey Recombinant Viruses Expressing Infectious Bursal Disease Virus (IBDV) VP2 Immunogen Induce Protection Against an IBDV Virulent Challenge in Chickens, Virology, 1995, 481-490, 211.
Dorsch-Häsler, K. et al., A long and complex enhancer activates transcription of the gene coding for the highly abundant immediate early mRNA in murine cytomegalovirus, Proc. Nat. Acad. USA, Dec. 1985, pp. 8325-8329, 82.
EP14196345-4, Application, drawings, sequence listing. Title "Immortalized chicken embryo fibroblasts". Applicant: Intervet International B.V.: pp. 1-32, Dec. 4, 2014.
European Search report for 14200340.9 dated Jul. 9, 2015, 6 pages.
International Search report for PCT/EP2015/081121 dated Mar. 8, 2016, 12 pages.
Sondermeijer, et al, Avian Herpesvirus as a Live Viral Vector for the Expression of Heterologous Antigens, Vaccine, 1993, 349-358, 11.
Tarpey, I. et al., A recombinant turkey herpesvirus expressing chicken interleukin-2 increases the protection provided by in ovo vaccination with infectious bursal disease and infectious bronchitis virus, Vaccine, 2007, pp. 8529-8535, 25.
Wu, et al., Molecular Detection and Differentiation of Infectious Bursal Disease Virus, Avian Diseases, 2007, 515-526, 51.
Cox, R.J. et al., Non-lethal viral challenge of influenza haemagglutinin and nucleoprotein DNA vaccinated mice results in reduced viral replication, Scand. J. Immunol., 2002, pp. 14-23, 55.

(Continued)

*Primary Examiner* — Antonio Galisteo Gonzalez

(57) ABSTRACT

The present invention regards a new and Improved HVT-vectored ND-IBD vaccine, comprising a recombinant HVT comprising the VP2 gene from IBDV and the F gene from NDV to a target animal. The recombinant HVT can be used in a vaccine for poultry, which displayed good viral vector replication, effective expression of the NDV F- and IBDV VP2 genes, improved immunoprotection against ND and IBD, and improved genetic stability over prior art constructs.

18 Claims, 4 Drawing Sheets

Figure 1:
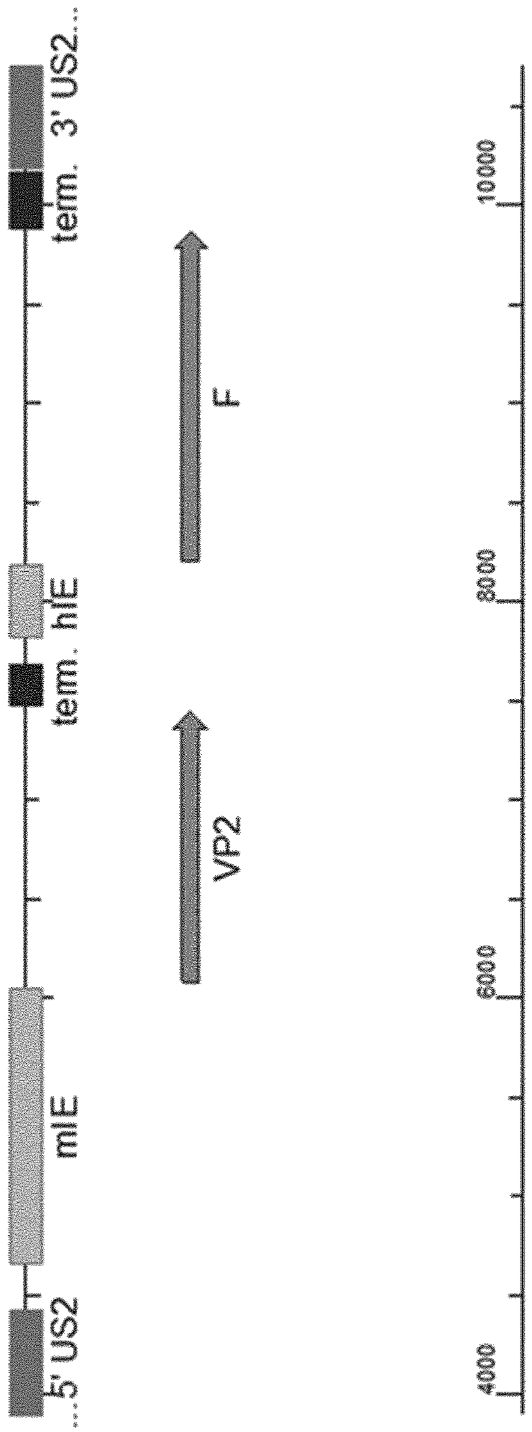

Specification includes a Sequence Listing.

(56) References Cited

OTHER PUBLICATIONS

Koedood, M. et al., Human Cytomegalovirus (HCMV) Immediate-Early Enhancer/Promoter Specificity during Embryogenesis Defines Target Tissues of Congenital HCMV Infection, Journal of Virology, 1995, pp. 2194-2207, Vo. 69, No. 4.
Kost, T.A., et al., The nucleotide sequence of the chick cytoplatic B-actin gene, Nucleic Acids Research, 1983, pp. 8287-8301, vol. 11, No. 23.
Petherbridge, et al., Cloning of Gallid Herpesvirus 3 (Marek's Disease Virus Serotype-2), Journal of Virological Methods, 2009, 11-17, 158.
Spatz, S.J. and Schat, K.A., Comparative genomic sequence analysis of the Marek's disease vaccine strain SB-1, Virus Genes, 2011, pp. 331-338, 42.
Tsukamoto, et al., Complete, Long-Lasting Protection Against Lethal Infectious Bursal Disease Virus Challenge by a Single Vaccination with an Avian Herepesvirus Vector Expressing VP2 Antigens, Journal of Virology, 2002, 5637-5645, 76-11.
Armour, N. and García, M., Current and Future Applications of Viral-Vectored Recombinant Vaccines in Poultry, The poultry informed professional, 2014, pp. 1-12, Issue 134.
Cui, H. et al, Avirulent Marek's disease virus type 1 strain 814 vectored vaccine expressing avian influenza (AI) virus H5 Haemagglutinin induced better protection than turkey herpesvirus vectored AI vaccine, PLOS One, Jan. 2013, pp. e533340 (and the next 9 pages), vol. 8, issue 1.
Gao, H. et al., Expression of HA of HPAI H5N1 Virus at US2 Gene Insertion Site of Turkey Herpesvirus Induced Better Protection than That at US10 Gene Insertion Site, Plos One, 2011, pp. e22549 and the next 8 pages., vol. 6, Issue 7.
Prokhorov, AM, The Great Soviet Encyclopedia, "Soviet Encyclopaedia" Publishing House, 1971, pp. 735-736, 3rd edition.
Schat, K.A., Back to the past: do vector vaccines represent the future?, 2015, pp. 1-12. Retrieved from the internet via URL: http://www.barnhealth.com/wp-content/uploads/2016/01/Vector_Vaccines_Dr.-Schat.pdf . No further bibliographic details are available for this reference.
Supotnitskiy M.V., Genotherapeutic vector systems based on viruses, Biopreparats (Biopharmaceuticals), 2011, pp. 15-26, No. 3.
Thornton, D.H., et al, Efficacy of Marek's disease vaccines: Protection and Viraemia studies with turkey herpes virus vaccines, Avian Pathology, 1975, pp. 97-108, 4:2.
Woo, Y.H. and Li, W-H., Gene clustering pattern, promoter architecture, and gene expression stability in eukaryotic genomes, PNAS, 2011, pp. 336-3311, vol. 108, No. 8.

SEQUENCE LISTING

<160> NUMBER OF SEQ ID NOS: 1

<210> SEQ ID NO 1
<211> LENGTH: 6674
<212> TYPE: DNA
<213> ORGANISM: Artificial Sequence
<220> FEATURE:
<223> OTHER INFORMATION: HVP360 expression cassette with flanking regions
<220> FEATURE:
<221> NAME/KEY: gene
<222> LOCATION: (1)..(399)
<223> OTHER INFORMATION: Upstream part of HVT Us2 gene; AF291866, nt 140143-140541
<220> FEATURE:
<221> NAME/KEY: promoter
<222> LOCATION: (630)..(2020)
<223> OTHER INFORMATION: murine cytomegalovirus immediate early 1 gene promoter-enhancer
<220> FEATURE:
<221> NAME/KEY: gene
<222> LOCATION: (2052)..(3410)
<223> OTHER INFORMATION: IBDV strain 52/70, VP2 gene
<220> FEATURE:
<221> NAME/KEY: polyA_signal
<222> LOCATION: (3441)..(3650)
<223> OTHER INFORMATION: SV40 polyA signal + terminator
<220> FEATURE:
<221> NAME/KEY: promoter
<222> LOCATION: (3805)..(4149)
<223> OTHER INFORMATION: Human cytomegalovirus immediate early 1 gene promoter core
<220> FEATURE:
<221> NAME/KEY: gene
<222> LOCATION: (4174)..(5835)
<223> OTHER INFORMATION: NDV Clone 30 F-gene
<220> FEATURE:
<221> NAME/KEY: terminator
<222> LOCATION: (5815)..(6127)
<223> OTHER INFORMATION: hCMV IE gene terminator
<220> FEATURE:
<221> NAME/KEY: gene
<222> LOCATION: (6156)..(6674)
<223> OTHER INFORMATION: Downstream part of HVT Us2 gene; AF291866, nt 140541-141059

<400> SEQUENCE: 1
atctactgtc ttaacgccca tgggaacgga ggcgtcgtcg tcatgtattg gacggcaaca 60
taggcagcaa cacaaattgc gtttaggtgg ggtgcatgtg gactcgatac caagcccctg 120
cagctgggga acgtctggtg gagagccgat aatttgatat acgcacgcca tattactgtc 180
gttgaagtac gccttatctt ctatgttttc aaatttaggt tcccaagtgg acgtgagaag 240
tgtttgtatc tcacatggaa tggcccaagg cattccagcc caggtgcctg gtactttaat 300
ggcaaacaaa cgttttggta gaggtattga ttctattgca gttctgcaga tatctgcagc 360
cccgagtatc cacaggctat acgatacgtt atcggaggca agctgcggcc gctctagaac 420
tagtggatcc cccgggctgc agcccaatgt ggaattcgcc cttgcacatt gttactcctg 480
catcttaaaa atatatcctg tagtaatttt cacagcaatg tcataacatc atctcgctaa 540
agaatgacct gggattggag aagtaatgaa tatttgcaac caatgcattg aataaactaa 600
cattaaacga attcactagt ggatccccca actccgcccg ttttatgact agaaccaata 660
gtttttaatg ccaaatgcac tgaaatcccc taatttgcaa agccaaacgc cccctatgtg 720
agtaatacgg ggactttttta cccaatttcc caagcggaaa gccccctaat acactcatat 780
ggcatatgaa tcagcacggt catgcactct aatggcggcc catagggact ttccacatag 840
ggggcgttca ccatttccca gcataggggt ggtgactcaa tggcctttac ccaagtacat 900

-continued

```
tgggtcaatg ggaggtaagc caatgggttt ttcccattac tggcaagcac actgagtcaa    960
atgggacttt ccactgggtt ttgcccaagt acattgggtc aatgggaggt gagccaatgg   1020
gaaaaaccca ttgctgccaa gtacactgac tcaataggga ctttccaatg ggtttttcca   1080
ttgttggcaa gcatataagg tcaatgtggg tgagtcaata gggactttcc attgtattct   1140
gcccagtaca taaggtcaat agggggtgaa tcaacaggaa agtcccattg gagccaagta   1200
cactgcgtca atagggactt tccattgggt tttgcccagt acataaggtc aataggggat   1260
gagtcaatgg gaaaaaccca ttggagccaa gtacactgac tcaataggga ctttccattg   1320
ggttttgccc agtacataag gtcaataggg ggtgagtcaa caggaaagtc ccattggagc   1380
caagtacatt gagtcaatag ggactttcca atgggttttg cccagtacat aaggtcaatg   1440
ggaggtaagc caatgggttt ttcccattac tggcacgtat actgagtcat tagggacttt   1500
ccaatgggtt ttgcccagta cataaggtca ataggggtga atcaacagga aagtcccatt   1560
ggagccaagt acactgagtc aatagggact ttccattggg ttttgcccag tacaaaaggt   1620
caatagggggg tgagtcaatg ggtttttccc attattggca cgtacataag gtcaataggg   1680
gtgagtcatt gggtttttcc agccaattta attaaaacgc catgtacttt cccaccattg   1740
acgtcaatgg gctattgaaa ctaatgcaac gtgaccttta aacggtactt tcccatagct   1800
gattaatggg aaagtaccgt tctcgagcca atacacgtca atgggaagtg aaagggcagc   1860
caaaacgtaa caccgccccg gttttcccct ggaaattcca tattggcacg cattctattg   1920
gctgagctgc gttctacgtg ggtataagag gcgcgaccag cgtcggtacc gtcgcagtct   1980
tcggtctgac caccgtagaa cgcagagctc ctcgctgcag gcggccgctc tagaactcgt   2040
cgatcgcagc gatgacaaac ctgcaagatc aaacccaaca gattgttccg ttcatacgga   2100
gccttctgat gccaacaacc ggaccggcgt ccattccgga cgacaccctg gagaagcaca   2160
ctctcaggtc agagacctcg acctacaatt tgactgtggg ggacacaggg tcagggctaa   2220
ttgtcttttt ccctggattc cctggctcaa ttgtgggtgc tcactacaca ctgcagagca   2280
atgggaacta caagttcgat cagatgctcc tgactgccca gaacctaccg gccagctaca   2340
actactgcag actagtgagt cggagtctca cagtgaggtc aagcacactc cctggtggcg   2400
tttatgcact aaacggcacc ataaacgccg tgaccttcca aggaagcctg agtgaactga   2460
cagatgttag ctacaatggg ttgatgtctg caacagccaa catcaacgac aaaattggga   2520
atgtcctggt aggggaaggg gtcactgtcc tcagcctacc cacatcatat gatcttgggt   2580
atgtgaggct tggtgacccc attcccgcta tagggcttga cccaaaaatg gtagctacat   2640
gcgacagcag tgacaggccc agagtctaca ccataactgc agccgatgat taccaattct   2700
catcacagta ccaaccaggt ggggtaacaa tcacactgtt ctcagccaac attgatgcta   2760
tcacaagcct cagcattggg ggagagctcg tgtttcaaac aagcgtccaa ggccttgtac   2820
tgggcgccac catctacctt ataggctttg atgggactgc ggtaatcacc agagctgtag   2880
ccgcagataa tgggctgacg gccggcaccg acaatcttat gccattcaat cttgtcattc   2940
caaccaatga gataacccag ccaatcacat ccatcaaact ggagatagtg acctccaaaa   3000
gtggtggtca ggcaggggat cagatgtcat ggtcggcaag tgggagccta gcagtgacga   3060
tccatggtgg caactatcca ggggccctcc gtcccgtcac actagtagcc tacgaaagag   3120
tggcaacagg atccgtcgtt acggtcgctg ggtgagtaa cttcgagctg attccaaatc   3180
ctgaactagc aaagaacctg gttacagaat acggccgatt tgacccagga gccatgaact   3240
acacaaaatt gatactgagt gagagggacc gtcttggcat caagaccgtc tggccaacaa   3300
```

-continued gggagtacac tgattttcgt gagtacttca tggaggtggc cgacctcaac tctcccctga 3360
agattgcagg agcatttggc ttcaaagaca taatccgggc tataaggagg taagcttgat 3420
ctagagcggc cgcggggatc cagacatgat aagatacatt gatgagtttg gacaaaccac 3480
aactagaatg cagtgaaaaa aatgctttat ttgtgaaatt tgtgatgcta ttgctttatt 3540
tgtaaccatt ataagctgca ataaacaagt taacaacaac aattgcattc attttatgtt 3600
tcaggttcag ggggaggtgt gggaggtttt ttcggatcct ctagagtcga caattatttc 3660
atttaataac atatagccca aagacctcta tgaacattta gtttcccgta tactcaacgg 3720
cgcgtgtaca cacaagggcg aattccacag tggatatcaa gcttaattaa gtaccgagct 3780
cgaattggcg cgccaggtca attccctggc attatgccca gtacatgacc ttatgggact 3840
ttcctacttg gcagtacatc tacgtattag tcatcgctat taccatggtg atgcggtttt 3900
ggcagtacat caatgggcgt ggatagcggt ttgactcacg gggatttcca agtctccacc 3960
ccattgacgt caatgggagt ttgttttggc accaaaatca acgggacttt ccaaaatgtc 4020
gtaacaactc cgccccattg acgcaaatgg gcggtaggcg tgtacggtgg gaggtctata 4080
taagcagagc tcgtttagtg aaccgtcaga tcgcctggag acgccatcca cgctgttttg 4140
acctccatag aagacaccgg gcgcgccgga tccatgggcc ccagaccttc taccaagaac 4200
ccagtaccta tgatgctgac tgtccgagtc gcgctggtac tgagttgcat ctgtccggca 4260
aactccattg atggcaggcc tcttgcggct gcaggaattg tggttacagg agacaaagcc 4320
gtcaacatat acacctcatc ccagacagga tcaatcatag ttaagctcct cccgaatctg 4380
cccaaggata aggaggcatg tgcgaaagcc cccttggatg catacaacag gacattgacc 4440
actttgctca ccccccttgg tgactctatc cgtaggatac aagagtctgt gactacatct 4500 ggaggggga gacaggggcg ccttataggc gccattattg gcggtgtggc tcttggggtt 4560
gcaactgccg cacaaataac agcggccgca gctctgatac aagccaaaca aaatgctgcc 4620
aacatcctcc gacttaaaga gagcattgcc gcaaccaatg aggctgtgca tgaggtcact 4680
gacggattat cgcaactagc agtggcagtt gggaagatgc agcagtttgt taatgaccaa 4740
tttaataaaa cagctcagga attagactgc atcaaaattg cacagcaagt tggtgtagag 4800
ctcaacctgt acctaaccga attgactaca gtattcggac cacaaatcac ttcacctgct 4860
ttaaacaagc tgactattca ggcactttac aatctagctg gtggaaatat ggattactta 4920
ttgactaagt taggtgtagg gaacaatcaa ctcagctcat taatcggtag cggcttaatc 4980
accggtaacc ctattctata cgactcacag actcaactct tgggtataca ggtaactcta 5040
ccttcagtcg ggaacctaaa taatatgcgt gccacctact tggaaacctt atccgtaagc 5100
acaaccaggg gatttgcctc ggcacttgtc ccaaaagtgg tgacacaggt cggttctgtg 5160
atagaagaac ttgacacctc atactgtata gaaactgact tagatttata ttgtacaaga 5220
atagtaacgt tccctatgtc ccctggtatt tattcctgct tgagcggcaa tacgtcggcc 5280
tgtatgtact caaagaccga aggcgcactt actacaccat acatgactat caaaggttca 5340
gtcatcgcca actgcaagat gacaacatgt agatgtgtaa accccccggg tatcatatcg 5400
caaaactatg gagaagccgt gtctctaata gataaacaat catgcaatgt tttatcctta 5460
ggcgggataa ctttaaggct cagtggggaa ttcgatgtaa cttatcagaa gaatatctca 5520
atacaagatt ctcaagtaat aataacaggc aatcttgata tctcaactga gcttgggaat 5580
gtcaacaact cgatcagtaa tgctttgaat aagttagagg aaagcaacag aaaactagac 5640

-continued

```
aaagtcaatg tcaaactgac tagcacatct gctctcatta cctatatcgt tttgactatc   5700
atatctcttg tttttggtat acttagcccg attctagcat gctacctaat gtacaagcaa   5760
aaggcgcaac aaaagacctt attatggctt gggaataata ctctagatca gatgagagcc   5820
actacaaaaa tgtgaggatc tctcgaggaa ttctagatcc cacgtcacta ttgtatactc   5880
tatattatac tctatgttat actctgtaat cctactcaat aaacgtgtca cgcctgtgaa   5940
accgtactaa gtctcccgtg tcttcttatc accatcaggt gacatcctcg cccaggctgt   6000
caatcatgcc ggtatcgatt ccagtagcac cggccccacg ctgacaaccc actcttgcag   6060
cgttagcagc gcccctctta acaagccgac ccccaccagc gtcgcggtta ctaacactcc   6120
tctccccgac ctgcaactag tgcggccgca gcttgcctcc gattctagca ttacatagcc   6180
ggtcagtaga tcctgccatt cggtagcgca accggctaca tcttcaaaca gtctcacgat   6240
aaatgcatct ctcgttcctg ccaatccgga accgggcata ccactcccgc ctgccgattt   6300
aattctcaca attgggcgat gccggcgggg caaaacgaat gtggatttgg caaaccgaca   6360
caggtctgct gtacggacta atatgggcac acccacatca ttcttcagat gctccatgca   6420
ttgttctatg agaaagatcc atagggtgga ggcagcgtca cgagatcgcc caggcaatcg   6480
atcgcattcg tctagtaaag tgacgagagt tatcatgcac acacccatgc ccacgccttc   6540
cgaataactg gagctgtgga agatcggaaa cgtctttttg actgccggtc tcgtactact   6600
ttcgcacagg tgtatacccg gacgcgtact atatatttta tatcatccaa cgtcccgaaa   6660
ttacatacgt ggcg                                                     6674
```

HVT-VECTORED ND-IBD VACCINE

CROSS-REFERENCE TO RELATED APPLICATIONS

This application is a national stage entry under 35 U.S.C. § 371 of PCT/EP2015/081121 filed on Dec. 23, 2015, which claims priority to EP Application No. EP14200340.9 filed on Dec. 24, 2014. The content of PCT/EP2015/081121 is hereby incorporated by reference in its entirety.

The present invention relates to the field of veterinary vaccines, namely to vaccines for poultry against ND and IBD, based on recombinant herpesvirus of turkeys (HVT) as viral vector. In particular the invention relates to a recombinant DNA expression cassette, to a recombinant HVT comprising the recombinant DNA expression cassette, to a vaccine for poultry based on the recombinant HVT or on host cells comprising the recombinant HVT. Further the invention relates to methods and uses of the expression cassette, the recombinant HVT, and the host cells, for the preparation and use of the vaccine.

Marek's disease (MD) is a highly infectious disease of poultry, occurring worldwide, and is characterized by the presence of T-cell lymphomas in several organs and nerves. This leads to a variety of symptoms, among others paralysis and mortality. New-born chicks can be protected by maternally derived antibodies (MDA) from immune mothers. MD is caused by Marek's disease virus (MDV) which belongs to the family alphaherpesvirideae, and the genus Mardivirus. The virion is enveloped and about 160 nm in size. Within the capsid is comprised a large genome of linear double stranded DNA, between 100 and 200 kbp in size.

There are different serotypes of MDV, each with distinct characteristics. While MDV serotype 1 (MDV1) and MDV2 are pathogenic to poultry, MDV3 is not. MDV3 is more commonly known as: Meleagrid herpesvirus 1, turkey herpesvirus, but typically as: herpesvirus of turkeys (HVT). HVT was described in 1970 (Witter et al., 1970, Am. J. Vet. Res., vol. 31, p. 525), as a herpesvirus of turkeys which is apathogenic to chickens. Strains of HVT such as PB1 or FC-126 have since then been commonly used to vaccinate chickens against MD caused by MDV1 or MDV2. And in case protection against more virulent variants of MDV1 is required, HVT is used in combination with an MDV2 vaccine-strain, for example SB1, as in Nobilis™ Marexine CA126+SB1 (MSD Animal Health), or with an attenuated MDV1 vaccine strain such as Rispens, e.g. in Nobilis™ RISMAVAC+CA126 (MSD Animal Health).

HVT replicates in the birds' peripheral blood lymphocytes (PBL's), and is thus a systemic virus which induces an immune response of long duration that is mostly aimed at the cellular immune system.

HVT vaccines are commercially available as frozen HVT-infected cells, and can be applied to chickens at an early age, as they are relatively insensitivity to antibodies against HVT such as in MDA. Because a new born chick faces infective pressure of MDV from its first day, therefore HVT vaccines are inoculated into chicks as early as possible; e.g. at the day of their hatching from the egg (day one), or even before hatching, while still in the egg. This last approach, so-called 'in ovo vaccination', is a form of embryo vaccination, which is commonly applied at day 18 of embryonic development (ED), about 3 days before hatch.

Next to being used as a vaccine per se, HVT is also used as a viral vector vaccine for the expression and delivery of various immunogenic proteins to poultry, see e.g. WO 87/04463. Typically the expressed gene encodes (a part of) a protective antigen of a micro-organism pathogenic to poultry, against which vaccination is required. Through the years many heterologous genes have been expressed in HVT vectors, such as from: Newcastle disease virus (NDV) (Sondermeijer et al., 1993, Vaccine, vol. 11, p. 349-358), infectious bursal disease virus (IBDV) (Darteil et al., 1995, Virology, vol. 211, p. 481-490), and of a parasite antigen (Cronenberg et al., 1999, Acta Virol., vol. 43, p. 192-197).

The administration of an HVT vector vaccine to poultry thus generates an immune response against the expressed heterologous gene, as well as against HVT which protects against MD. This is applied in a variety of commercial HVT vector vaccine products, for instance: the NDV F protein gene: Innovax™-ND (MSD Animal Health), and Vectormune™ HVT-NDV (Ceva); or the IBDV VP2 gene: Vaxxitek™ HVT+IBD (Merial; previously named: Gallivac™ HVT-IBD), and Vectormune™ HVT-IBD (Ceva).

Alternatively an HVT vector can be used for the expression and delivery of a therapeutic protein, e.g. a cytokine, to manipulate the chicken's immune response (WO 2009/156.367; Tarpey et al., 2007, Vaccine, vol. 25, p. 8529-8535).

The genomic nucleotide sequence of HVT is available, for example from GenBank™ as: AF291866 (strain FC-126). Several methods have been described for inserting heterologous genes into HVT, such as by using homologous recombination (Sondermeijer et al., supra), Cosmid regeneration (U.S. Pat. No. 5,961,982), or Bacmids (bacterial artificial chromosomes) (Baigent et al., 2006, J. of Gen. Virol., vol. 87, p. 769-776).

Many genetic locations for the insertion of a heterologous gene-construct into the HVT genome have been investigated, and several suitable, non-essential loci have been described, e.g. in the unique short (Us) region of the HVT genome (EP 431.668); or in the HVT unique long (UL) region (EP 794.257).

Different promoters have been used to drive the expression of a heterologous gene in an expression cassette for HVT, such as: the PRV gpX promoter (WO 87/04.463), the Rous sarcoma virus LTR promoter, the SV40 early gene promoter, the chicken beta-actin gene promoter (EP 1.298.139), or the immediate early1 gene promoter from human (hCMV IE1) or murine (mCMV 1E1) cytomegalovirus, see: EP 728.842. Recently an HVT vector vaccine was described that expressed antigens from both NDV and IBDV from a single construct: WO 2013/057.235.

For the construction of recombinant vectors, the heterologous nucleic acid that is to be inserted into the vector's genome, usually comprises at least one heterologous gene or coding region, which encodes (at least an immunogenic part of) an antigen. Also the construct may comprise a promoter sequence to drive the expression of the heterologous gene, and regulatory signals such as an enhancer, or a transcription terminator. Such a combined insert is often termed an 'expression cassette'.

The effect of the insertion of an expression cassette into a vector's genome differs, depending on the location and on the way it is inserted: the vector genome may become larger, the same, or smaller in size, depending from whether the net result on the genome is an addition, replacement or deletion of genetic material, respectively. Also the location of the insertion may have an effect: placed inside a coding-, a non-coding, or a regulatory region of the genome. Among others, these choices influence the characteristics of the resulting vector vaccine, in terms of its ability for replication and expression, and its genetic stability.

Whatever the precise construct, the inserted expression cassette must allow the live recombinant viral vector to overcome a number of biological stresses upon its stability and efficacy: first, the capability of replication and generating progeny after having received the heterologous insert. This indicates the recombinant vector virus itself is still viable, in spite of the insertion into its genome. Next, the capability to replicate in vitro in a host cell-line for many cycles while maintaining the replication and expression of the heterologous insert, correctly and completely. This indicates the recombinant was not attenuated in its replication by the insertion, and the inserted expression cassette is stably maintained and expressed. Thirdly, replication and expression in vivo. This indicates the recombinant virus can overcome the strong selection pressure in a live animal, such as posed by its immune system. In this environment the loss of expression of a heterologous gene by the vector would favour a faster replication in the animal; such 'escape mutants' can have acquired mutations or major deletions in the foreign gene or in its regulatory sequences, and this mutant could overgrow the intact virus vectors. Finally, and most importantly, the vector's replication and the heterologous gene's expression in the target, need to be able to generate an effective immune response against the micro-organism that was the donor of the heterologous insert that the vector expresses.

Consequently, a recombinant vector vaccine must provide a good replication of the vector and of its insert, both in vitro and in vivo, and an effective expression of the heterologous gene(s) in vivo, preferably of high level, and consistent over time, to induce and maintain a protective immune-response in a target.

This combination of features will allow for the extensive rounds of replication in vitro that are necessary for large scale production, as well as for the continued expression and presentation to the host's immune system of the inserted foreign gene, when the vector vaccine is replicating in an inoculated target animal. In addition, this stability in replication and in expression is required of the vector vaccine to comply with the very high standards of safety and biological stability that must be met by a recombinant virus that is to be introduced into the field as a commercial product, after obtaining a marketing authorisation from governmental or regulatory authorities.

Newcastle disease (ND) and infectious bursal disease (IBD) are important diseases of poultry, which occur worldwide, and can cause severe negative effects in the poultry industry regarding animal welfare and economy of operation. This is described e.g. in handbooks, like: The Merck veterinary manual (2010, 10th ed., 2010, C. M. Kahn edt., ISBN: 091191093X), and: 'Disease of poultry' (2008, 12$^{th}$ ed., Y. Saif ed., Iowa State Univ. press, ISBN-10: 0813807182).

ND is caused by Newcastle disease virus (NDV), which belongs to the order of the Mononegavirales, specifically of the family Paramyxoviridae, and can be grouped into distinct pathotypes according to their virulence: the non-pathogenic lentogenic type NDV's hardly cause symptoms in poultry. In contrast, the mesogenic (medium pathogenic) and velogenic (highly pathogenic) NDV strains cause extensive disease and mortality, and are therefore notifiable diseases in many countries. Disease symptoms include respiratory and nervous abnormalities, with gasping and 'torticollis' as most notable signs.

In commercial poultry operations, protection against infection and/or disease caused by pathogenic NDV strains is achieved by routine vaccination of poultry, typically at day of hatch, with live lentogenic NDV strains, such as Nobilis™ ND Clone 30 (MSD Animal Health).

NDV has a non-segmented, negative sense, single stranded RNA genome, which is about 15 kb in size, and contains six genes, amongst which is the gene for the fusion (F) glycoprotein. The F protein is involved in NDV's attachment of—and entry into host cells, and as the immunodominant protein it can be the basis of an effective immune response against NDV. The NDV F protein is expressed as a native FO protein, which is activated upon cleavage by extra-cellular peptidases.

IBD is caused by infectious bursal disease virus (IBDV), also called 'Gumboro disease virus', a member of the Birnaviridae family. These viruses have a genome consisting of two segments (A and B) of double-stranded RNA. The larger segment A encodes a polyprotein of 110 kDa, which is subsequently cleaved by autoproteolysis to form mature viral proteins VP2, VP3 and VP4. Of these, VP2 and VP3 are the structural capsid proteins for the virion, and VP2 is the major host-protective immunogen.

In the case of IBDV, two serotypes exist, serotype 1 and 2. The two serotypes can be differentiated by virus neutralisation (VN) tests. Serotype 1 viruses have been shown to be pathogenic to chickens, while serotype 2 IBDV only causes sub-acute disease in turkeys.

Historically, IBDV serotype 1 viruses consisted of only one type that is known as "classic" IBD virus. More recent, so-called "variant" IBDV strains emerged, which can be identified and distinguished by a virus neutralisation test using a panel of monoclonal antibodies or by RT-PCR; this is reviewed by Wu et al. (2007, Avian Diseases, vol. 51, p. 515-526). Well-known classic IBDV strains are: D78, Faragher 52/70, and STC.

IBDV causes an acute, highly-contagious viral infection of a bird's lymphoid tissue, with as its primary target the bird's essential immunological organ: the bursa of Fabricius. The morbidity rate in susceptible flocks is high, with rapid weight loss and moderate to high mortality rates. Birds that recover from the disease may have immune deficiencies because of destruction of (parts of) the bursa of Fabricius. This makes them vulnerable to secondary infections.

Routine vaccinations against IBD are performed as early as possible in the life of poultry using attenuated IBDV strains, but these can only be applied when the level of MDA against IBDV has decreased enough, which commonly is somewhere between 15 and 20 days post hatch. Many 'live' or inactivated IBDV vaccines are commercially available, e.g. a 'live' vaccine such as Nobilis™ Gumboro D78 (MSD Animal Health).

To achieve cost efficiency, a common approach is to design veterinary vaccines that comprise a combination of antigens. In this way a single vaccination round can immunise the animal against a number of diseases at once. Not only does this save time and labour costs, but it also reduces discomfort and stress to the vaccinated animals that would otherwise occur from having to receive repeated vaccinations. This is even more applicable to vaccines that need to be administered by individual injection, such as vaccines based on recombinant HVT as viral vector, therefore combination vaccines in this context are also highly desirable, and the ability to protect against several different diseases at once—in addition to MDV protection from the HVT vector itself—would be a great benefit. However in the past, the mere combination of two separate HVT vectors with single heterologous gene inserts turned out unsuccessful: interference between the replicating vectors caused one or the other to become suppressed in the vaccinated target. Therefore research has focussed on the combined expression and delivery of more than one heterologous antigen from a single recombinant HVT vector.

Several publications describe HVT vector constructs that comprise multi-gene inserts, for example: in WO 93/025.665 and WO 96/005.291, describing bivalent and trivalent 'vaccines'. Similarly: EP 719.864, and EP 1.026.246. However most of the described multi-gene constructs are only suggested, and only some of the recombinant vectors with multiple inserts were actually constructed and isolated. Very few were ever tested in chickens. Overall no results are given on their stability upon replication, or the expression levels of the foreign genes, let alone any data on the induction of an effective immune protection in target animals.

In fact, from the many prior art publications on multigene HVT-vectored vaccines, the only constructs that have been thoroughly tested and were demonstrated to be effective vector vaccines against more than two avian pathogens, are the HVT construct comprising the NDV F gene and the IBDV VP2 gene, as described in WO 2013/057.235, and the HVT vectored ILT-ND vaccine as described in WO 2013/057.236.

Unfortunately, upon prolonged testing during product development, one of the main constructs as described in WO 2013/057.235, named HVP309, did not display adequate genetic stability and sustained expression of heterologous inserts. This HVP309 recombinant HVT vector comprises an expression cassette with the NDV F gene, driven by a human cytomegalovirus immediate early 1 gene core promoter, followed downstream by an IBDV VP2 gene that is driven by a chicken beta-actin gene core promoter.

The instability of the HVP309 vector construct became apparent after its replication in vitro and in vivo, as between 1 and 3% of HVP309 virus displayed they no longer expressed one or both of the heterologous genes. This is undesirable from a vaccine efficacy standpoint, and it is an obstacle for gaining marketing authorisation from governmental authorities. Therefore, there currently is still no safe and effective HVT vector vaccine against both ND and IBD that has consistent and reliable genetic stability.

It is an object of the present invention to accommodate to this need in the field, and to provide, for the first time, a recombinant HVT vector vaccine that allows the effective immunisation of poultry against ND and IBD, and that has consistent and reliable genetic stability.

Initially the inventors were disappointed to learn that the HVP309 construct had this inherent genetic instability, leading to loss of expression of its heterologous gene inserts. Without guidance from the prior art on ways to overcome this instability—while maintaining vaccine efficacy and viral replication levels—they had to completely redesign a vector vaccine.

This was not at all straightforward and required making unobvious choices and selections. This is apparent from the many recombinant HVT constructs that were made and tested, but did not show the desired combination of favourable characteristics. While occasionally one of the new constructs was better in a specific aspect, such as vireamia, or expression level of one of the inserted genes; however this was then found to lack in other properties, or did not have adequate genetic stability. Examples are described hereinafter.

The inventors were therefore surprised to find that one specific recombinant HVT vaccine demonstrated good viral vector replication, a sustained NDV F—and IBDV VP2 gene expression, and effective immunoprotection against ND and IBD, and also has an improved genetic stability over prior art constructs. In fact the stability is now such that no non-expressing virus plaques can be found anymore, even after 15 consecutive passages in cell-culture, and after one passage in birds. In addition, the level of vaccine efficacy against ND and IBDV was slightly (ND) or even considerably (IBDV) improved relative to previous vector constructs.

In view of the potentially large scale at which such a vector vaccine may be used in the poultry producing industry, these effects and improvements are significant, and represent a surprising technical effect that has great commercial significance. Therefore, in this way the object of the invention can be met, and consequently disadvantages of the prior art can be overcome.

It is currently not known why the new recombinant HVT vectored ND-IBD vaccine has the improved efficacy and improved stability characteristics.

Although the inventors do not want to be bound by any theory or model that might explain these observations, they speculate that the selection of elements used, and their specific layout in the expression cassette comprised in this HVT virus, in one way or other allows the new recombinant HVT vector to better accommodate the expression of the heterologous genes, while replicating in vitro, or in vivo. This may be what makes the new vector genetically stable and immunologically effective.

Therefore in a first aspect the invention relates to a recombinant DNA expression cassette comprising in 5' to 3' direction and in this order:

a. a murine cytomegalovirus immediate early 1 gene (mCMV-IE1) promoter,
b. an infectious bursal disease virus (IBDV) viral protein 2 (VP2) gene,
c. a transcription terminator,
d. a human cytomegalovirus immediate early 1 gene (hCMV-IE1) promoter,
e. a Newcastle disease virus (NDV) fusion (F) protein gene.

The recombinant DNA expression cassette according to the invention can be used for the generation of a recombinant HVT vector virus vaccine, which is effective in preventing or reducing infection by IBDV, and NDV, or associated signs of disease, and has consistent and reliable genetic stability, both when passaged in vitro and in vivo.

A "recombinant" is a nucleic acid molecule, or a microorganism of which the genetic material has been modified relative to its starting—or native condition, to result in a genetic make-up that it did not originally possess.

The "expression cassette" for the invention comprises the genes and regulatory elements as described and defined herein. Optionally the expression cassette may also contain other DNA elements that can assist in its generation and manipulation, such as sites for restriction enzyme recognition or PCR primers, to enable molecular cloning. While the expression cassette can exist in DNA or in RNA form, because of its intended use in a HVT vector, therefore the expression cassette is employed as DNA.

As will be apparent to a skilled person, an expression cassette is a self-contained expression module, therefore its orientation in a vector virus genome is generally not critical. That means that the cassette as a whole can be integrated e.g. into the Us region of the HVT genome in either of two orientations: reading either towards the TRs, or towards the IRs. FIG. 1 in that respect only displays one of these two possible orientations. However if a specific orientation is desired, the expression cassette can be used with flanking sections from the genome of the vector, which can direct its integration at a specific locus of the vector's genome, and in a desired orientation.

The generation, construction and assembly of the recombinant DNA expression cassette according to the invention, and of other genetic elements described herein, can be done by well-known molecular biological techniques, involving cloning, transfection, recombination, selection, and amplification. These, and other techniques are explained in great detail in standard text-books like Sambrook & Russell: "Molecular cloning: a laboratory manual" (2001, Cold Spring Harbour Laboratory Press; ISBN: 0879695773); Ausubel et al., in: Current Protocols in Molecular Biology (J. Wiley and Sons Inc, NY, 2003, ISBN: 047150338X); C. Dieffenbach & G. Dveksler: "PCR primers: a laboratory manual" (CSHL Press, ISBN 0879696540); and "PCR protocols", by: J. Bartlett and D. Stirling (Humana press, ISBN: 0896036421).

The term "comprising" (as well as variations such as "comprise", "comprises", and "comprised") as used herein, intends to refer to all elements, and in any possible combination conceivable for the invention, that are covered by or included in the text section, paragraph, claim, etc., in which this term is used, even if such elements or combinations are not explicitly recited; and not to the exclusion of any of such element(s) or combinations.

Therefore any such text section, paragraph, claim, etc., can therefore also relate to one or more embodiment(s) wherein the term "comprising" (or its variants) is replaced by terms such as "consist of", "consisting of", or "consist essentially of".

The term "in 5' to 3' direction", also known as: in downstream direction', is well known in the field. Together with the terms "in this order" it serves to indicate the relative orientation which the elements that are summed up thereafter need to have in respect of each other, in order to be functional with the gene-expression machinery of the host cell in which a recombinant HVT comprising the expression cassette according to the invention will be replicated and expressed. As the skilled person will realise, this direction relates to the DNA strand from the double stranded DNA genome of HVT that is the 'coding strand', and it relates to the encoded mRNA molecule that is in the '+' or 'sense' orientation.

Nevertheless, and without prejudice to the section above: on the complementary strand of the HVT ds DNA genome, the 'template' strand, the relative order of the listed elements is the same, but on that DNA strand the direction of these elements is 3' to 5'.

The term "gene" is used to indicate a section of DNA that is capable of encoding a protein. A gene for the invention preferably encodes a complete protein. However, a gene may also encode a section of a protein, for example encoding only the mature form of a protein, i.e. without a 'leader', 'anchor', or 'signal sequence'. In that respect gene as used herein corresponds to open reading frame or ORF. A gene may even encode a specific section of a protein, such as the section comprising an immunoprotective epitope.

In this regard a "protein" for the invention is a molecular chain of amino acids. The protein can be a native or a mature protein, a pre- or pro-protein, or a functional fragment of a protein. Inter alia: peptides, oligopeptides and polypeptides are included within the definition of protein.

A "promoter" for the invention is well known to be a functional region on the genome of an organism that directs the transcription of a downstream coding region. A promoter is thus situated upstream of a gene.

The mRNA synthesis directed by the promoter, starts from the 'transcription start site' (TSS). The mRNA produced is in turn translated into protein starting from the gene's startcodon, which is the first ATG sequence in the open reading frame (the first AUG in the mRNA). Typically the TSS is located at 30-40 nucleotides upstream of the start codon. A TSS can be determined by sequencing the 5' end of the mRNA of a gene, e.g. by the RACE technique.

In general promoters are comprised within about 1000 nucleotides upstream of the position of the A of the startcodon, which is generally indicted as A+1, and most promoters are situated between nucleotides −500 and A+1.

The nomenclature for a promoter is commonly based on the gene of which it controls the expression. For example, the term 'mCMV-1E1 gene promoter', refers to the promoter that in nature drives the expression of the IE1 gene from mCMV, and is thus situated immediately upstream of that gene. Because the IE1-gene is such a well-documented and clearly recognisable gene, and because the genomes of several mCMV have been sequenced (in whole or in part), such a promoter can readily be identified by routine techniques. For example, in a basic protocol a promoter can simply be obtained by roughly subcloning the region in between two consecutive genes, e.g. from the poly A signal of an upstream gene to the TSS of a downstream gene. The promoter can then be identified by standard tests, e.g. by the expression of a marker gene by progressively smaller sections of a suspected promoter.

Commonly promoters contain a number of recognisable, regulatory regions, such as the enhancer region, which is involved in binding regulatory factors that influence the time, the duration, the conditions, and the level of transcription. While the enhancer region is commonly situated upstream, a promoter also contains a region more downstream that is involved in the binding of transcription factors and directing the RNA polymerase itself. This downstream region generally contains a number of conserved promoter sequence elements such as the TATA box, the CAAT box, and the GC box.

A promoter comprising both the enhancer—and the downstream region is termed a "complete" promoter; a promoter comprising only the downstream region, is termed a "core" promoter.

A promoter for the expression of a (heterologous) gene in a (virus) vector needs to be able to effectively drive the transcription of that downstream coding region. This is commonly referred to as the promoter being "operatively linked" to the gene, such that the gene is 'under the control' of the promoter, or is 'driven by' the promoter. This commonly means that in the expression cassette the promoter and the gene are connected on the same DNA, in effective proximity, and with no signals or sequences between them that would intervene with an effective transcription.

Therefore, in the recombinant DNA expression cassette according to the invention, the mCMV-IE1 gene promoter and the hCMV-IE1 gene promoter for the invention are "operatively linked" to their downstream genes, respectively the IBDV VP2 gene, and the NDV F gene.

A "transcription terminator" is a regulatory DNA element involved in the termination of the transcription of a coding region into RNA. Commonly such an element encodes a section with a secondary structure, e.g. a hairpin, that can cause the RNA polymerase complex to strop transcription. A transcription terminator is therefore always situated downstream of the stop codon from the region to be translated, the 3' untranslated region. A terminator can also comprise a poly-adenylation signal, or polyA signal. This induces the polyadenylation that occurs to most eucaryotic mRNA's, and which is relevant for the transportation and stability of mRNA molecules.

For the invention, the use of a transcription terminator in-between the two heterologous genes, provides for an effective separation of their expression, preventing possible read-through of RNA transcription.

For the invention, a gene is "heterologous" to the recombinant HVT vector that carries it, if that gene was not present in the parental HVT that was used to generate the recombinant HVT vector.

The mCMV-IE1—or the hCMV-IE1 gene promoters are well known in the art, and can be readily obtained from a variety of commercial sources, such as from suppliers of commercial plasmids for cloning and expression. The IE1 gene is also called the 'major IE gene'.

The mCMV-IE1 protein is also called pp89. The mCMV IE1 gene promoter was described in 1985 (K. Dörsch-Häsler, et al., 1985, PNAS, vol. 82, p. 8325). Use of this promoter in heterologous expression is described in WO 87/03.905 and EP 728.842. The nucleotide sequence of the complete mCMV IE locus is available from GenBank under acc. nr. L06816.1 (from March 2004). The mCMV itself is available from the ATCC: initially under acc. nr. VR-194, and more recently this has been continued under acc. nr. VR-1399.

The hCMV-IE1 gene promoter in its complete version is about 1,5 kb in size and consists of an enhancer, a core promoter, and an intron, whereby the promoter activity proceeds into the intron region, see Koedood et al. (1995, J. of Virol., vol. 69, p. 2194-2207).

An hCMV-IE1 gene promoter can be obtained from the genome of an hCMV virus (which are widely available), by subcloning the genomic area preceding the IE1 gene, using routine molecular biological tools and methods. Alternatively the promoter can be derived for example from expression type plasmids, such as p117, described by Cox et al. (2002, Scand. J. Immunol., vol. 55, p. 14-23), or from mammalian expression vectors such as the pCMV (Clontech), or pCMV-MCS series (Stratagene; GenBank™ acc. nr. AF369966).

From the hCMV-IE1 gene promoter, many highly similar versions are known, e.g. from GenBank. Such homologs and variants are within the scope of the invention.

An "NDV F protein gene" for the invention is well known and sequence information is extensively available in the prior art. The F protein gene can be obtained from a variety of commonly available plasmid constructs. Alternatively, it can be obtained from an NDV isolated from nature, using routine techniques for manipulating an RNA virus. NDV can be readily identified using serology, or molecular biology.

For the invention homologs of the NDV F protein gene would equally be applicable, as well as variants e.g. from lentogenic, mesogenic of velogenic type NDV, as the F protein gene sequence itself is highly conserved in these different NDV pathotypes.

In an embodiment of the expression cassette according to the invention, the mCMV-IE1 gene promoter is a complete promoter, comprising both the core promoter region, as well as the enhancer region for the mCMV-IE1 gene. The complete mCMV-IE1 gene promoter is about 1.4 kb in size.

As the skilled person is well aware, some variance in length may occur, either of the mCMV 1E1-gene promoter but also of the other elements that make up the recombinant DNA expression cassette according to the invention. This can result from differences in the exact conditions that are used for cloning and construction; for example from using different restriction enzyme sites, PCR cloning primers, or different conditions for adapting the ends of the cloning molecules used. Consequently, some variation in length—smaller or larger—of the constituting elements may occur, without affecting the stability and efficacy of the overall expression cassette. In that case these length differences are immaterial, and are within the scope of the invention.

Therefore in regard to the mCMV-IE1 gene promoter for the invention, "about 1.4 kb" is: 1.4 kb ±about 25%, preferably ±about 20, 15, 12, 10, 8, 6, 5, 4, 3, 2, or even ±about 1%, in that order of preference.

Similarly, homologs or variants of the promoter element may be used that are equally effective and stable.

Therefore, in an embodiment the mCMV-IE1 gene promoter for the invention is a DNA molecule of about 1.4 kb, comprising a nucleotide sequence that has at least 95% nucleotide sequence identity to the full length of the region of nucleotides 630-2020 of SEQ ID NO: 1. More preferred is a nucleotide sequence identity of at least 96, 97, 98, or even 99%, in that order of preference.

In an embodiment, the mCMV-IE1 gene promoter is the region of nucleotides 630-2020 of SEQ ID NO: 1.

In an embodiment of the expression cassette according to the invention, the IBDV VP2 gene for the invention encodes a VP2 protein from an IBDV that is of the classic type. Such genes are well known and their sequence information is readily available in the prior art, see e.g. GenBank acc.nr: D00869 (F52/70), D00499 (STC), or AF499929 (D78). Alternatively, this gene can be obtained from the genome of a classic IBDV isolated from nature, using routine techniques for manipulating a Birnavirus. Classic type IBDV's can be readily identified using serology, or molecular biology.

As homologs or variants of the IBDV VP2 gene may have equal efficacy and stability, therefore in an embodiment, the IBDV VP2 protein gene for the invention has at least 90% nucleotide sequence identity to the full length of the region of nucleotides 2052-3410 of SEQ ID NO: 1. Preferably a nucleotide sequence identity of at least 92, 94, 95, 96, 97, 98, or even 99%, in that order of preference.

In an embodiment the IBDV VP2 protein gene for the invention is derived from the classic IBDV strain Faragher 52/70.

In an embodiment the IBDV VP2 protein gene for the invention is the region of nucleotides 2052-3410 of SEQ ID NO: 1.

For the expression cassette according to the invention, the selection of a specific type of transcription terminator is not critical, as long as effective termination of RNA transcription is provided.

In an embodiment of the expression cassette according to the invention, the transcription terminator comprises both a terminator region and a polyA region.

In an embodiment the transcription terminator is derived from simian virus 40 (SV40), preferably from the SV40 late gene. This terminator and its use in heterologous expression, has been applied in molecular virology for many years, and was commercialised by Clontech with their 'pCMVβ' cloning plasmids, that are commercially available since the end of the 1980's.

In an embodiment, the transcription terminator is derived from the SV40 late gene and is about 0.2 kb in size.

As the exact size is not critical, therefore, in regard to the transcription terminator for the invention, "about 0.2 kb" is: 0.2 kb ±about 25%, preferably ±about 20, 15, 12, 10, 8, 6, 5, 4, 3, 2, or even ±about 1%, in that order of preference.

In an embodiment the transcription terminator derived from the SV40 late gene and about 0.2 kb in size, comprises a nucleotide sequence that has at least 95% nucleotide sequence identity to the full length of the region of nucleotides 3441-3650 of SEQ ID NO: 1. More preferred is a nucleotide sequence identity of at least 96, 97, 98, or even 99%, in that order of preference.

In an embodiment, the transcription terminator from the SV40 late gene is the region of nucleotides 3441-3650 of SEQ ID NO: 1.

In an embodiment of the expression cassette according to the invention, the hCMV-IE1 gene promoter is a core promoter. Such a core promoter will typically be smaller than 1 kb in size; preferably about 0.4 kb in size.

As described, the exact size is not critical, therefore, in regard to the hCMV-IE1 gene core promoter for the invention, "about 0.4 kb" is: 0.4 kb ±about 25%, preferably ±about 20, 15, 12, 10, 8, 6, 5, 4, 3, 2, or even ±about 1%, in that order of preference.

In an embodiment the hCMV-IE1 gene promoter for the invention is a DNA molecule of about 0.4 kb, comprising a nucleotide sequence that has at least 95% nucleotide sequence identity to the full length of the region of nucleotides 3789-4149 of SEQ ID NO: 1. More preferred is a nucleotide sequence identity of at least 96, 97, 98, or even 99%, in that order of preference.

In an embodiment, the hCMV-IE1 gene core promoter is the region of nucleotides 3789-4149 of SEQ ID NO: 1.

In an embodiment of the expression cassette according to the invention, the NDV F protein gene is from an NDV that is of the lentogenic type.

Preferably the NDV F protein gene from a lentogenic NDV strain is from NDV strain Clone 30.

In an embodiment, the NDV F protein gene for the invention has at least 90% nucleotide sequence identity to the full length of the region of nucleotides 4174-5835 of SEQ ID NO: 1. Preferably a nucleotide sequence identity of at least 92, 94, 95, 96, 97, 98, or even 99%, in that order of preference.

In an embodiment the NDV F protein gene for the invention is the region of nucleotides 4174-5835 of SEQ ID NO: 1.

In an embodiment, the expression cassette according to the invention comprises an additional transcription terminator which is located downstream of the NDV F protein gene.

The additional transcription terminator, located downstream of the NDV F protein gene, may be the same or different compared to the transcription terminator that is in the expression cassette according to the invention, in between the IBDV VP2 protein gene and the hCMV-IE1 promoter, as long as proper transcription termination is provided, and stability and expression are not affected.

In an embodiment, the additional transcription terminator is derived from the hCMV-IE1 gene. Preferably the additional transcription terminator is about 0.3 kb in size.

As the exact size is not critical, therefore, in regard to the additional transcription terminator derived from the hCMV-IE1 gene, "about 0.3 kb" is: 0.3 kb ±about 25%, preferably ±about 20, 15, 12, 10, 8, 6, 5, 4, 3, 2, or even ±about 1%, in that order of preference.

In an embodiment the additional transcription terminator derived from the hCMV-IE1 gene, and about 0.3 kb in size, comprises a nucleotide sequence that has at least 95% nucleotide sequence identity to the full length of the region of nucleotides 5847-6127 of SEQ ID NO: 1. More preferred is a nucleotide sequence identity of at least 96, 97, 98, or even 99%, in that order of preference.

In an embodiment, the additional transcription terminator derived from the hCMV-IE1 gene is the region of nucleotides 5847-6127 of SEQ ID NO: 1.

In an embodiment of the recombinant DNA expression cassette according to the invention, one or more or all of the conditions apply selected from the group consisting of:

the mCMV-IE1 gene promoter is a complete promoter, the IBDV VP2 gene encodes a VP2 protein from a classic type IBDV, the transcription terminator comprises both a terminator region and a polyA region, the transcription terminator is derived from simian virus 40 (SV40), the hCMV-IE1 gene promoter is a core promoter, the NDV F gene is from a lentogenic NDV strain, the expression cassette comprises an additional transcription terminator which is located downstream of the NDV F gene, and the additional transcription terminator is derived from the hCMV-IE1 gene.

In an embodiment, the recombinant DNA expression cassette according to the invention comprises 5' and/or 3' flanking regions from a gene from HVT. These flanking regions allow for homologous recombination to direct the insertion to a target genetic insertion locus on the vector's genome, and in a desired orientation.

In a preferred embodiment the recombinant DNA expression cassette according to the invention is flanked on both sides by sections of the HVT Us2 gene.

An example is the DNA sequence as represented in SEQ ID NO: 1.

TABLE 1

| Elements of SEQ ID NO: 1: | | |
|---|---|---|
| Nucleotide region | | Element |
| 1 | 399 | 5' part of HVT Us2 gene |
| 630 | 2020 | mCMV-IE1 gene promoter-enhancer |
| 2052 | 3410 | IBDV strain F 52/70, VP2 gene |
| 3441 | 3650 | SV40 late gene terminator + polyA signal |
| 3789 | 4149 | hCMV-IE1 gene core promoter |
| 4174 | 5835 | NDV Clone 30 F-gene |
| 5847 | 6127 | hCMV IE gene terminator |
| 6156 | 6674 | 3' part of HVT Us2 gene |

In an embodiment, the recombinant DNA expression cassette according to the invention is about 5.5 kb in size. Because—as described—the exact size is not critical, therefore, in regard to the recombinant DNA expression cassette according to the invention, its size is about 5.5 kb, meaning 5.5 kb ±about 25%, preferably ±about 20, 15, 12, 10, 8, 6, 5, 4, 3, 2, or even ±about 1%, in that order of preference.

As described, homologs or variants of the elements of the recombinant DNA expression cassette according to the invention may be equally safe, stable and effective.

Therefore in an embodiment, the recombinant DNA expression cassette according to the invention is a DNA molecule of about 5.5 kb, comprising a nucleotide sequence that has at least 95% nucleotide sequence identity to the full length of the region of nucleotides 630-6127 of SEQ ID NO: 1. More preferred is a nucleotide sequence identity of at least 96, 97, 98, or even 99%, in that order of preference.

In an embodiment, the recombinant DNA expression cassette according to the invention is the region of nucleotides 630-6127 of SEQ ID NO: 1.

To facilitate the convenient construction, manipulation, and use of the recombinant DNA expression cassette according to the invention, this can itself be comprised in a DNA molecule.

Therefore, in a further aspect, the invention relates to a recombinant DNA molecule comprising the recombinant DNA expression cassette according to the invention.

In an embodiment the recombinant DNA molecule according to the invention consists of a cloning plasmid comprising the recombinant DNA expression cassette according to the invention. Examples of common cloning plasmids are e.g. plasmids from the pBR322, or pUC, series. These are widely commercially available.

In an embodiment of a plasmid that is the recombinant DNA molecule according to the invention, the plasmid can contain regulatory sequences that allow the stable maintenance of large inserts, and that control the plasmids' copy number upon amplification in bacteria to a low number. Such cloning plasmids for large inserts are commonly known as: Cosmids, or Bacmids.

When the recombinant DNA molecule according to the invention is to be used in transfection protocols, it is commonly referred to as a 'transfervector', 'shuttle vector', or 'donor plasmid'. In this situation the recombinant DNA molecule according to the invention comprises the recombinant DNA expression cassette according to the invention, and the cassette may be flanked on both sides by sequences derived from the vector's genome, to direct the insertion.

Typically, a transfervector that is used in transfection is not itself integrated into the genome of the vector, it only facilitates the integration of the expression cassette it carries.

In an embodiment the recombinant DNA molecule according to the invention comprises the region of nucleotides 630-6127 of SEQ ID NO: 1.

In an embodiment the recombinant DNA molecule according to the invention comprises the DNA molecule as presented in SEQ ID NO: 1.

The recombinant DNA expression cassette according to the invention is preferably used for the generation of a recombinant HVT vector virus vaccine.

Therefore in a further aspect, the invention relates to a recombinant herpes virus of turkeys (HVT), comprising a recombinant DNA expression cassette according to the invention, whereby the expression cassette is inserted in the Us region of the genome of the recombinant HVT.

The term "herpes virus of turkeys" (HVT) refers to a viral micro-organism that displays the characterising features of its taxonomic group-members such as the morphologic, genomic, and biochemical characteristics, as well as the biological characteristics of that group, such as in their physiologic, immunologic, or pathologic behaviour. This also includes HVT that are sub-classified in any way, for instance as a subspecies, strain, isolate, genotype, variant, subtype, serotype, pathotype, or subgroup and the like.

It will be apparent to a skilled person that the current taxonomic classification of a micro-organism described herein, such as an HVT, MDV, NDV, or IBDV for the invention, could change in time as new insights lead to reclassification into a new or different taxonomic group. However, as this does not change the micro-organism itself or its biological behaviour, but only its scientific name or classification, such re-classified micro-organisms remain within the scope of the invention.

For the invention, "comprising a recombinant DNA expression cassette" relates to the insertion of the recombinant DNA expression cassette according to the invention, into the genome of an HVT. This insertion can in principle be made by any available technique, and can result in an insertion, a substitution or a deletion, relative to the HVT vector's genome, provided the resulting recombinant HVT is able to display its favourable effects of safe, stable and effective multivalent antigen expression. Details and examples are described herein below.

The recombinant HVT according to the invention comprises the recombinant DNA expression cassette according to the invention in a single genetic locus, and in the region of its genome that is known as the Unique short region, or Us. The Us region of an HVT is well known and readily identifiable; it is situated between two well-known repeated elements in the HVT genome, the IRS and the TRS.

Several insertion loci are known for the HVT Us region, and in principle these are all suitable for use in the invention, provided the inserted expression cassette and the resulting recombinant HVT are able to display their stable and effective properties.

In an embodiment the recombinant HVT according to the invention comprises the recombinant DNA expression cassette according to the invention inserted in the Us2 or in the Us10 gene of the genome of the recombinant HVT.

Particularly stable and effective recombinant HVT vectors for the invention could be made by employing the Us2 gene of the HVT genome as the single genetic insertion locus for the invention.

Therefore, in an embodiment of the recombinant HVT according to the invention, the recombinant DNA expression cassette according to the invention is inserted in the Us2 gene of the genome of the recombinant HVT.

For the invention the terms "in the Us2 gene" or "in the Us10 gene" intend to indicate that an insertion has been made in the region of the HVT genome comprising the Us2 respectively the Us10 gene; this can refer to the gene's promoter or to its coding region. Also, the netto effect of the insertion relative to the HVT genome, may be an insertion, a substitution or a deletion, as described. An expected consequence of such insertion is that the normal coding function of the Us2 resp. Us10 gene is disturbed, or even completely abolished in the resulting recombinant HVT.

In an embodiment the insertion of the recombinant DNA expression cassette in the HVT Us region is an insertion; i.e. apart from a few nucleotides that may be missing or be replaced as a result of the cloning process, no substantial deletion in the Us genome region occurs. Consequently, with the netto increase in size, this way the resulting recombinant HVT has a genome size that is larger than the genome of its parent.

In an embodiment, the recombinant HVT according to the invention comprises a DNA molecule of about 5.5 kb, comprising a nucleotide sequence that has at least 95% nucleotide sequence identity to the full length of the region of nucleotides 630-6127 of SEQ ID NO: 1. More preferred is a nucleotide sequence identity of at least 96, 97, 98, or even 99%, in that order of preference.

In an embodiment, the recombinant HVT according to the invention comprises the region of nucleotides 630-6127 of SEQ ID NO: 1.

In an embodiment the recombinant HVT according to the invention comprises a nucleotide sequence as presented in SEQ ID NO: 1.

To make the recombinant HVT according to the invention safe for vaccine use, the recombinant HVT can be based on a parental HVT that is an established HVT vaccine strain that replicates well, and is known to be suitable for inoculation of young birds or embryos, for example the HVT vaccine strains PB1 or FC-126. These are generally available: FC-126 from ATCC: VR #584-C, and PB1 is commercially available e.g. from MSD Animal Health. The incorporation of the recombinant DNA expression cassette according to the invention does not increase the virulence or pathogenicity of the parental HVT (on the contrary), and no reversion to virulence is to be expected, as HVT are naturally apathogenic.

Therefore, in an embodiment the parental HVT used for generation of the recombinant HVT according to the invention is an HVT vaccine strain; preferably an HVT vaccine strain of the PB1 or the FC-126 strain.

The recombinant HVT according to the invention is a live recombinant carrier micro-organism, or a "vector" virus, which can advantageously be used for vaccination of poultry. It combines the features of being a safe and effective vaccine against ND and IBD, and in addition is genetically stable.

Being "genetically stable" for the invention means that the genetic make-up of the recombinant HVT according to the invention does not change in subsequent rounds of virus replication, or at least does not change to an extent that would be detectable. In the alternative, unstable constructs can lead to the loss of expression of one or both of the inserted heterologous gene(s). This stability can conveniently be monitored with routine techniques, e.g. by subjecting the recombinant HVT according to the invention to subsequent passaging in cell culture, followed by a passage in animals. Virus re-isolated during these steps, can be plated on cell culture dishes, covered with agar, and incubated until HVT specific plaques become visible; all using routine techniques. Next the plaques can be stained for expression of the F or the VP2 protein using suitable antibody preparations in an immunofluorescence assay (IFA) protocol, and adequate positive and negative controls. The number of plaques that do not show fluorescence can be recorded, whereby at least 100 individual plaques of a particular sample should be monitored.

A stringent test for genetic stability of the recombinant HVT according to the invention, is to apply 15 consecutive tissue culture passages, followed by an inoculation into target animals, re-isolation, and challenge-infection. Details are described hereinafter.

It was surprisingly found that the recombinant HVT according to the invention in a stringent stability test as described above, maintained the presence and the expression of both NDV F and the IBDV VP2 protein genes, in all of the plaques tested, and for 15 cell-culture passages, as well as for one animal passage. Details are described in the Examples.

This is a strong and highly significant improvement over results found with prior art HVT recombinants, and over other recombinants made and tested in the course of the experiments for the invention.

The recombinant HVT according to the invention can be amplified by common techniques, mainly by replication in in vitro cultures of primary chicken cells, typically chicken embryo fibroblast cells (CEF's). These can be prepared by trypsinisation of chicken embryos, all well-known in the art. The CEF's are plated in monolayers and infected with the HVT. This process can be scaled up to industrial size production.

Commonly the recombinant HVT is collected by harvesting the infected host cells that contain the recombinant HVT in its cell-associated form. These cells are taken up in an appropriate carrier composition to provide stabilisation during freezing and storage. Next the infected cells are commonly filled into glass ampoules, which are sealed, frozen and stored in liquid nitrogen.

Although cell-associated frozen storage of HVT is preferred, in situations where use of liquid nitrogen is not feasible, an alternative is to use freeze-drying: this employs the favourable characteristic of HVT that it can be isolated from its host cell by cell-disruption, e.g. by French press or sonifier, using the whole culture. This can be clarified by centrifugation, and is then taken up into a stabiliser, and freeze dried for prolonged storage.

Therefore, in a further aspect, the invention relates to a host cell comprising a recombinant HVT according to the invention.

A "host cell" for the invention, is a cell that is susceptible to infection and replication by an HVT. Examples of such cells are avian cells, and in particular lymphocytes, or fibroblasts.

In an embodiment, the host cell according to the invention is a primary avian cell; i.e. a cell that is derived directly from an animal or an animal organ, and not from a cell-line. Typically primary cells can only perform a small and limited number of cell-divisions, whereas cells from a cell-line are effectively immortal, and—under the correct conditions—can keep on dividing.

In an embodiment the primary avian host cell according to the invention is a primary chicken embryo fibroblast (CEF).

In an embodiment, the host cell according to the invention is an immortalised avian cell. Several immortalised avian cells have been described, for example in WO 97/044.443 and WO 98/006.824.

In a preferred embodiment the immortalised avian host cell according to the invention is an immortalised CEF; preferably an immortalised CEF as described in EP 14196345.

By different methods of cloning and transfection, the recombinant DNA expression cassette according to the invention can be used to obtain the recombinant HVT according to the invention, comprising the expression cassette stably integrated in the Us region of the genome of the recombinant HVT.

Therefore, a further aspect of the invention relates to a method for the construction of a recombinant HVT according to the invention, said method comprising the insertion of a recombinant DNA expression cassette according to the invention, into the Us region of the genome of the recombinant HVT.

The insertion of the recombinant DNA expression cassette according to the invention into an HVT genome to generate the recombinant HVT according to the invention, can be performed in different ways, all known in the art. One convenient way is to use a transfervector; in an embodiment this can be the recombinant DNA molecule according to the invention.

The direct insertion of the recombinant DNA expression cassette according to the invention into an HVT genome is the preferred method to generate a recombinant HVT according to the invention. However there are other well-known ways in which such a recombinant HVT can be generated. For example by indirect insertion, whereby parts of the expression cassette are inserted into HVT in single or in multiple round(s) of transfection. These parts can be devised in such a way that upon integration of all parts, the total insert forms the complete expression cassette, for example by employing overlapping regions to steer the order and the orientation of the parts. An alternative is the use of Bacmids, as described in EP 996.738.

The preferred insertion technique to generate a recombinant HVT according to the invention, is by using cosmid regeneration, e.g. as described in WO 93/25.665. This technique essentially employs a set of large overlapping sub-genomic fragments of the HVT genome to reconstruct a complete HVT genome by cotransfection into host cells. As one of the cosmids is made to comprise the recombinant DNA expression cassette according to the invention, this becomes stably integrated into the genome of the recombinant HVT.

As described, the preferred use of the recombinant HVT according to the invention, is in a vaccine for poultry.

Therefore in a further aspect the invention relates to a vaccine for poultry comprising a recombinant HVT according to the invention, and/or a host cell according to the invention, and a pharmaceutically acceptable carrier.

A “vaccine” is well known to be a composition comprising an immunologically active compound, in a pharmaceutically acceptable carrier. The ‘immunologically active compound’, or ‘antigen’ is a molecule that is recognised by the immune system of the inoculated target and induces an immunological response. The response may originate from the innate or the acquired immune system, and may be of the cellular and/or the humoral type.

The vaccine according to the invention provides a safe and early protection of chickens against ND and IBD. This effect is obtained by preventing or reducing the establishment or the proliferation of a productive infection by a field-infection with NDV or IBDV in their respective target organs. This is achieved for example by reducing the viral load or shortening the duration of the viral replication. In turn this leads to a reduction in the target animal of the number, the intensity, or the severity of lesions and associated clinical signs of disease caused by the viral infection. Such a vaccine is colloquially referred to as a vaccine ‘against’ NDV, or IBDV.

In addition to vaccine efficacy against ND and IBD, the vaccine according to the invention is also effective against MD, because of the vaccination capacity by the HVT itself. This is not diminished by the insertion of the recombinant DNA expression cassette according to the invention into the Us region. However, depending on the virulence of the MDV field virus in a certain area, it may be necessary to add a further MD vaccine component, as described, in order to be fully efficacious as a vaccine against MDV.

The determination of the effectiveness of a vaccine according to the invention, is well within the skills of the routine practitioner, and can be done for instance by monitoring the immunological response following vaccination or by testing the appearance of clinical symptoms or mortality after a challenge infection, e.g. by monitoring the targets’ signs of disease, clinical scores, serological parameters, or by re-isolation of the challenge pathogen, and comparing these results to a vaccination-challenge response seen in mock vaccinated animals. To assess vaccine efficacy against ND, challenge survival is a convenient measurement; for IBD, clinical signs of disease in the bursa can conveniently be used.

Various embodiments, preferences and examples of a vaccine according to the invention will be outlined below.

The term “poultry” for the invention relates to a species of bird of relevance to veterinary practice, and that is susceptible to inoculation with HVT; the preferred poultry species are: chicken, turkey, and quail. Chickens are the most preferred species.

For the invention, the poultry may be of any type, breed, or variety, such as: layers, breeders, broilers, combination breeds, or parental lines of any of such breeds. Preferred types are: broiler, breeder, and layer. Most preferred are broiler chickens, as for this type of birds the early protection against ND and IBD results in the improvement of survival, growth rate and feed conversion.

A “pharmaceutically acceptable carrier” is intended to aid in the stabilisation and administration of the vaccine, while being harmless and well-tolerated by the target. Such a carrier can for instance be sterile water or a sterile physiological salt solution. In a more complex form the carrier can e.g. be a buffer, which can comprise further additives, such as stabilisers or conservatives. Details and examples are for instance described in well-known handbooks such as: “Remington: the science and practice of pharmacy” (2000, Lippincott, USA, ISBN: 683306472), and: “Veterinary vaccinology” (P. Pastoret et al. ed., 1997, Elsevier, Amsterdam, ISBN 0444819681).

For the present invention, when the vaccine is cell-associated HVT, then the pharmaceutically acceptable carrier is preferably a mixture of culture medium, and about 10% serum, and about 6% DMSO. The serum can be any serum routinely used for cell culturing such as foetal—or new-born calf serum.

The vaccine according to the invention is prepared from a recombinant HVT according to the invention by methods as described herein, which are readily applicable by a person skilled in the art. For example, the recombinant HVT according to the invention is constructed by insertion of a recombinant expression cassette according to the invention by transfection and recombination. Next the desired recombinant HVT is selected, and is amplified industrially in smaller or larger volumes, preferably in in vitro cell cultures, e.g. in CEF's. From such cultures a suspension comprising the virus is harvested, either as whole infected cells or as a cell-free preparation, obtained by cell-disruption. This suspension is formulated into a vaccine and the final product is packaged. Cell-associated vaccine is then stored in liquid nitrogen and freeze-dried vaccine at −20 or at +4° C. After extensive testing for quality, quantity and sterility the vaccine product is released for sale.

General techniques and considerations that apply to the preparation of vaccines are well known in the art and are described for instance in governmental regulations (Pharmacopoeia) and in handbooks such as: "Veterinary vaccinology" and: "Remington" (both supra).

In an embodiment the vaccine according to the invention is a cell-associated vaccine.

"Cell-associated" meaning comprising host cells according to the invention, that are infected with a recombinant HVT according to the invention. Consequently a vaccine of this type comprises both host cells as well as recombinant HVT, both according to the invention.

In an embodiment, the vaccine according to the invention is a cell-free virus vaccine.

"Cell-free" meaning comprising the recombinant HVT according to the invention, and being substantially free of host cells according to the invention. The cell-free vaccine can however contain (very) small amounts of host cell-fragments, remaining from the cell-disruption process. The cell-free vaccine is preferably in freeze dried form. Procedures for freeze-drying are known to persons skilled in the art, and equipment for freeze-drying at different scales is available commercially.

Therefore, in an embodiment, the cell-free virus vaccine according to the invention is in a freeze-dried form.

To reconstitute a freeze-dried vaccine, it is suspended in a physiologically acceptable diluent. This is commonly done immediately before administration, to ascertain the best quality of the vaccine. The diluent can e.g. be sterile water, or a physiological salt solution. The diluent to be used for reconstituting the vaccine can itself contain additional compounds, such as an adjuvant.

In a further embodiment of the freeze dried cell-free vaccine according to the invention, the diluent for the vaccine is supplied separately from the freeze dried cake comprising the active vaccine composition. In this case, the freeze dried vaccine and the diluent composition form a kit of parts that together embody the vaccine according to the invention.

Therefore, in a preferred embodiment of the freeze dried cell-free vaccine according to the invention, the vaccine is a kit of parts with at least two types of containers, one container comprising the freeze dried vaccine, and one container comprising a watery diluent.

The target animal for the vaccine according to the invention can in principle be healthy or diseased, and may be positive or negative for presence of NDV or IBDV, or for antibodies against NDV or IBDV. Also the target can be of any weight, sex, or age at which it is susceptible to the vaccination. However it is evidently favourable to vaccinate healthy, uninfected targets, and to vaccinate as early as possible to prevent any field infection and its consequences.

A vaccine according to the invention can thus be used either as a prophylactic—or as a therapeutic treatment, or both, as it interferes both with the establishment and with the progression of an infection by NDV or IBDV.

In that respect, a further advantageous effect of the reduction of viral load by the vaccine according to the invention, is the prevention or reduction of shedding and thereby the spread of the virus, both vertically to offspring, and horizontally within a flock or population, and within a geographical area. Consequently, the use of a vaccine according to the invention leads to a reduction of the prevalence of NDV or IBDV.

Therefore further aspects of the invention are:

the use of a vaccine according to the invention for reducing the prevalence of NDV or IBDV in a population or in a geographical area, and the vaccine according to the invention for reducing the prevalence of NDV or IBDV in a population or in a geographical area.

The vaccine according to the invention in principle can be given to target poultry by different routes of application, and at different points in their lifetime, provided the inoculated recombinant HVT can establish a protective infection.

However, because an infection with NDV or IBDV can be established already at very young age, it is advantageous to apply the vaccine according to the invention as early as possible. Therefore the vaccine according to the invention can be applied at the day of hatch ("day 1"), or in ovo, e.g. at 18 days ED.

Therefore, in an embodiment, the vaccine according to the invention is administered in ovo.

Equipment for automated injection of a vaccine into an egg at industrial scale, is available commercially. This provides the earliest possible protection, while minimising labour cost. Different in ovo inoculation routes are known, such as into the yolk sac, the embryo, or the allantoic fluid cavity; these can be optimised as required. Preferably in ovo inoculation is performed such that the needle actually touches the embryo.

In an embodiment, the vaccine according to the invention is administered by parenteral route. Preferably by intramuscular—or subcutaneous route.

A vaccine according to the invention can be prepared in a form that is suitable for administration to a poultry target, and that matches with the desired route of application, and with the desired effect.

Preferably a vaccine according to the invention is formulated as an injectable liquid, suitable for injection, either in ovo, or parenteral; for example as: a suspension, solution, dispersion, or emulsion. Commonly such vaccines are prepared sterile.

Depending on the route of application of the vaccine according to the invention, it may be necessary to adapt the vaccine's composition. This is well within the capabilities of a skilled person, and generally involves the fine-tuning of the efficacy or the safety of the vaccine. This can be done by adapting the vaccine dose, quantity, frequency, route, by using the vaccine in another form or formulation, or by adapting the other constituents of the vaccine (e.g. a stabiliser or an adjuvant).

For example, to be suitable for application in ovo, the vaccine composition is required to be very safe, in order not to reduce the hatchability of the eggs. However, even then some reduction in hatchability may still occur, e.g. resulting from mechanical damage to the embryo by the inoculation itself, or an infection, etc.

The exact amount of recombinant HVT according to the invention per animal dose of the vaccine according to the invention is not as critical as it would be for an inactivated type vaccine; this because the recombinant HVT can replicate and thus multiply in the target animal up to a level of vireamia that is biologically sustainable. In principle the vaccine dose only needs to be sufficient to initiate such a productive infection. A higher inoculum dose does not shorten the time it takes to reach an optimal vireamic infection in the host. Therefore, very high doses are not effective and in addition are not attractive for economic reasons.

A preferred inoculum dose is therefore between 1×10^1 and 1×10^5 plaque forming units (pfu) of recombinant HVT according to the invention per animal-dose, more preferably between 1×10^2 and 1×10^4 pfu/dose, even more preferably between 500 and 5000 pfu/dose; most preferably between about 1000 and about 3000 pfu/dose.

When the vaccine according to the invention is cell-associated, these amounts of recombinant HVT are comprised in infected host cells.

Methods to count viral particles of the recombinant HVT according to the invention are well known.

The volume per animal dose of the recombinant HVT according to the invention can be optimised according to the intended route of application: in ovo inoculation is commonly applied with a dose of between about 0,01 and about 0.5 ml/egg, and parenteral injection is commonly done with a dose of between about 0.1 and about 1 ml/bird.

Determination of what is an immunologically effective amount of the vaccine according to the invention, or the optimisation of the vaccine's volume per dose, are both well within the capabilities of the skilled artisan.

The dosing regimen for applying the vaccine according to the invention to a target organism can be in single or multiple doses, in a manner compatible with the formulation of the vaccine, and in such an amount as will be immunologically effective.

Preferably, the regimen for the administration of a vaccine according to the invention is integrated into existing vaccination schedules of other vaccines that the target poultry may require, in order to reduce stress to the animals and to reduce labour costs. These other vaccines can be administered in a simultaneous, concurrent or sequential fashion, in a manner compatible with their registered use.

It goes without saying that admixing other compounds, such as stabilisers, carriers, adjuvants, diluents, emulsions, and the like to vaccines according to the invention are also within the scope of the invention. Such additives are described in well-known handbooks such as: "Remington", and "Veterinary Vaccinology" (both supra).

This way the efficacy of a vaccine according to the invention, to protect poultry with a single inoculation at very young age against ND, IBD, and MD, can be further optimised.

The vaccine according to the invention effectively is a 'marker vaccine' for NDV and for IBDV, because the immunity it generates is only directed against one protein from these viruses. This allows for the "differentiation of infected and vaccinated animals", the so-called DIVA approach. This can conveniently be detected by a serological assay such as an ELISA or immuno-fluorescence assay.

The vaccine according to the invention already provides multiple immunity: against NDV and IBDV by the expression of the heterologous inserts, and in addition against MDV by the HVT vector itself. Nevertheless it can be advantageous to make further combinations by additional immunoactive components. This can serve to enhance the immune protection already provided, or to expand to other pathogens.

Therefore, in an embodiment, the vaccine according to the invention comprises at least one additional immunoactive component.

Such an "additional immunoactive component" may be an antigen, an immune enhancing substance, a cytokine, a vaccine, or any combination thereof. This provides advantages in terms of cost, efficiency and animal welfare. Alternatively, the vaccine according to the invention, may itself be added to a vaccine.

In an embodiment the at least one additional immunoactive component is an immunostimulatory compound; preferably a cytokine or an immunostimulatory oligodeoxynucleotide.

The immunostimulatory oligodeoxynucleotide is preferably an immunostimulatory non-methylated CpG-containing oligodeoxynucleotide (INO). A preferred INO is an avian Toll-like receptor (TLR) 21 agonist, such as described in WO 2012/089.800 (X4 family), WO 2012/160.183 (X43 family), or WO 2012/160.184 (X23 family).

In an embodiment the at least one additional immunoactive component is an antigen which is derived from a micro-organism pathogenic to poultry. This can be 'derived' in any suitable way, for instance as a 'live' attenuated, an inactivated, or a subunit antigen from that micro-organism pathogenic to poultry.

The additional antigen derived from a micro-organism pathogenic to poultry, is preferably derived from one or more micro-organism selected from the following groups consisting of:

viruses: infectious bronchitis virus, NDV, Adenovirus, Egg drop syndrome virus, IBDV, chicken anaemia virus, avian encephalo-myelitis virus, fowl pox virus, turkey rhinotracheitis virus, duck plague virus (duck viral enteritis), pigeon pox virus, MDV, avian leucosis virus, ILTV, avian pneumovirus, and Reovirus;

bacteria: *Escherichia coli, Salmonella, Ornitobacterium rhinotracheale, Haemophilus paragallinarum, Pasteurella multocida, Erysipelothrix rhusiopathiae, Erysipelas, Mycoplasma*, and *Clostridium;* parasites: Eimeria; and fungi: *Aspergillus.*

The additional antigen may be a further HVT-vector vaccine.

All these combinations are possible provided the efficacy, safety and stability of the vaccine according to the invention is not influenced negatively.

In an embodiment of the vaccine according to the invention, the additional antigen derived from a micro-organism pathogenic to poultry is a 'live' attenuated MDV, NDV, or IBDV vaccine strain. This serves to improve and expand the immunogenicity of the vaccine according to the invention, and this is advantageous in those cases or geographic areas where very virulent field strains of MDV, NDV or IBDV are prevalent.

In this regard, the combination of an HVT with an MDV1, MDV2, or HVT is known; for the invention an MDV of strain Rispens (MDV1), strain SB1 (MDV2), or strains FC-126 or PB1 (HVT) is preferred as additional immunoactive component.

To improve the response against NDV, the recombinant HVT according to the invention may be combined with an NDV vaccine strain such as the mild live NDV vaccine strain C2.

Similarly, to improve the response against IBDV, the recombinant HVT according to the invention may be combined with a mild live IBDV vaccine strains such as D78, PBG98, Cu-1, ST-12 or 89-03.

As the skilled person will appreciate, these 'combinations' also include vaccination schedules wherein the recombinant HVT according to the invention and the additional immunoactive component are not applied simultaneous, but concurrent or sequential; e.g. the recombinant HVT may be applied in ovo, the NDV C2 at day one, and the IBDV 89-03 strain at day 17.

Therefore, in an embodiment of the vaccine according to the invention comprising at least one additional immunoactive component, the at least one additional immunoactive component is a micro-organism selected from the group consisting of a vaccine strain from: MDV, NDV and IBDV, or any combination thereof.

More preferably the additional immunoactive component is selected from the group consisting of: MDV Rispens, MDV SB1, NDV C2, IBDV D78 and IBDV 89-03.

Such combination vaccines can be made in a variety of ways: by combining of preparations of virus or host cells, or a mixture of these; all are within the scope of the invention. In a preferred embodiment, the components for such a combination vaccine are conveniently produced separately and then combined by filling into the same vaccine container.

By the methods described above, and exemplified hereinafter, a vaccine according to the invention can be prepared.

Therefore, a further aspect of the invention relates to a method for the preparation of the vaccine according to the invention, said method comprising the steps of:

- infecting host cells with a recombinant HVT according to the invention,
- harvesting the infected host cells, and
- admixing the harvested infected host cells with a pharmaceutically acceptable carrier.

Suitable host cells and pharmaceutically acceptable carriers for the invention have been described above. Also, suitable methods for infection, culture and harvesting are well known in the art and are described and exemplified herein.

As outlined above in detail, the recombinant HVT according to the invention can advantageously be applied in a vaccine for poultry, providing a safe, stable and effective vaccination against MD, ND and IBD or associated signs of disease, and can be administered to poultry at a very young age.

Therefore, a further aspect of the invention relates to the recombinant HVT according to the invention, for use in a vaccine for poultry.

The different aspects and embodiments of 'use in a vaccine' of the recombinant HVT according to the invention have been outlined above, and comprise the use as cell-free or as cell-associated virus in different vaccine compositions for inoculation of poultry.

Consequently, the different aspects and embodiments of the invention can advantageously be used to produce a safe, stable and effective vaccine for poultry.

Therefore, in a further aspect, the invention relates to the use of an expression cassette, a recombinant DNA molecule, a recombinant HVT, or a host cell, all according to the invention, or any combination thereof, for the manufacture of a vaccine for poultry.

As described above, and as exemplified hereinafter, the vaccine according to the invention can advantageously be used to prevent or reduce infection by IBDV and/or NDV, or associated signs of disease, by a single inoculation at very young age.

Therefore further aspects of the invention are:

- the use of a vaccine according to the invention, for preventing or reducing infection by IBDV and/or NDV, or associated signs of disease.
- a method for preventing or reducing infection by IBDV and/or NDV, or associated signs of disease, the method comprising the administration of a vaccine according to the invention to poultry.
- a method of vaccination of poultry, comprising the step of inoculating said poultry with a vaccine according to the invention.

Details on the use of the vaccine according to the invention, by inoculation of poultry have been described above; specifically the inoculation by intramuscular or subcutaneous inoculation of day old chicks, and the in ovo inoculation of 18 day old embryos.

The invention will now be further described with reference to the following, non-limiting, examples.

EXAMPLES

1. The Different Expression Cassette Insertions Tested

Figure 2:
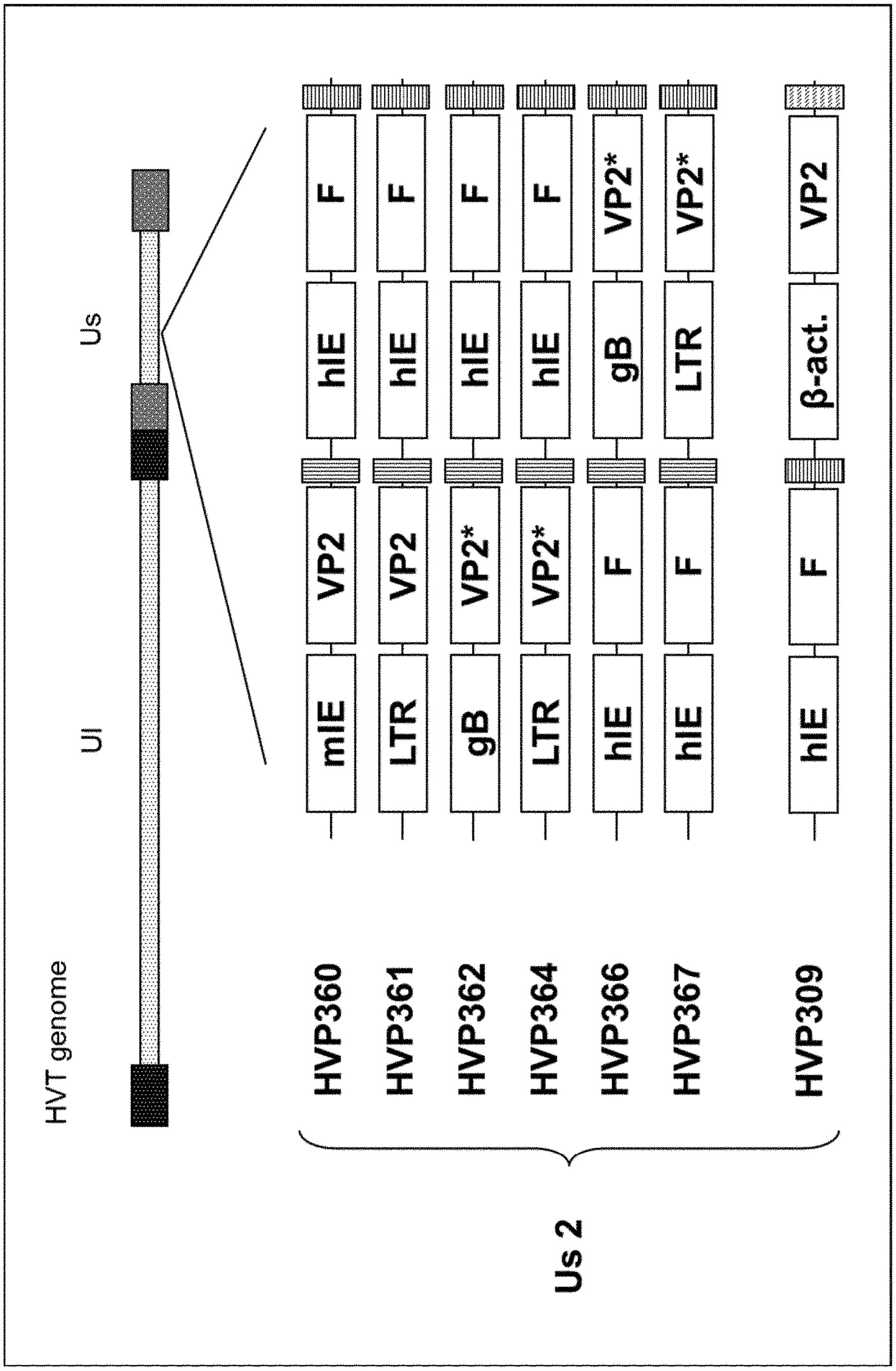

In the search for stable and effective recombinant HVT that expressed both NDV F and IBDV VP2, the inventors constructed a series of recombinant HVT constructs with different expression cassettes inserted in Us2, using different elements and orientations. In FIG. 2 a graphic representation is given (not drawn to scale), of the relevant elements of a representative number of similar constructs tested. For comparison the prior art construct HVP309 is also represented.

Variations tested were in the order of the protein genes, in the different promoters used, and in the type of insert gene used.

In more detail: the IBDV VP2 gene was connected to the following promoters:

- the mCMV 1E1 gene promoter (including enhancer—and core regions),
- the Long Terminal Repeat (LTR) promoter from the 3' terminal end of Rous Sarcoma Virus (Schmidt-Ruppin D strain), and
- the gB gene promoter from pseudorabies virus, from vaccine strain Bartha (GenBank acc. nr: BK001744)

Also, the VP2 gene was tested in a native and in a codon optimised version, using the HVT codon table.

Further in a number of constructs, the heterologous genes were in reversed order to each other.

All these different recombinant HVT were constructed, transfected, and amplified. Next they were selected by testing for expression in vitro on CEF cells, and for expression and vireamia in vivo by inoculation into experimental animals.

2. Vireamia and Serology of Different Recombinant HVT Constructs

Figure 3:
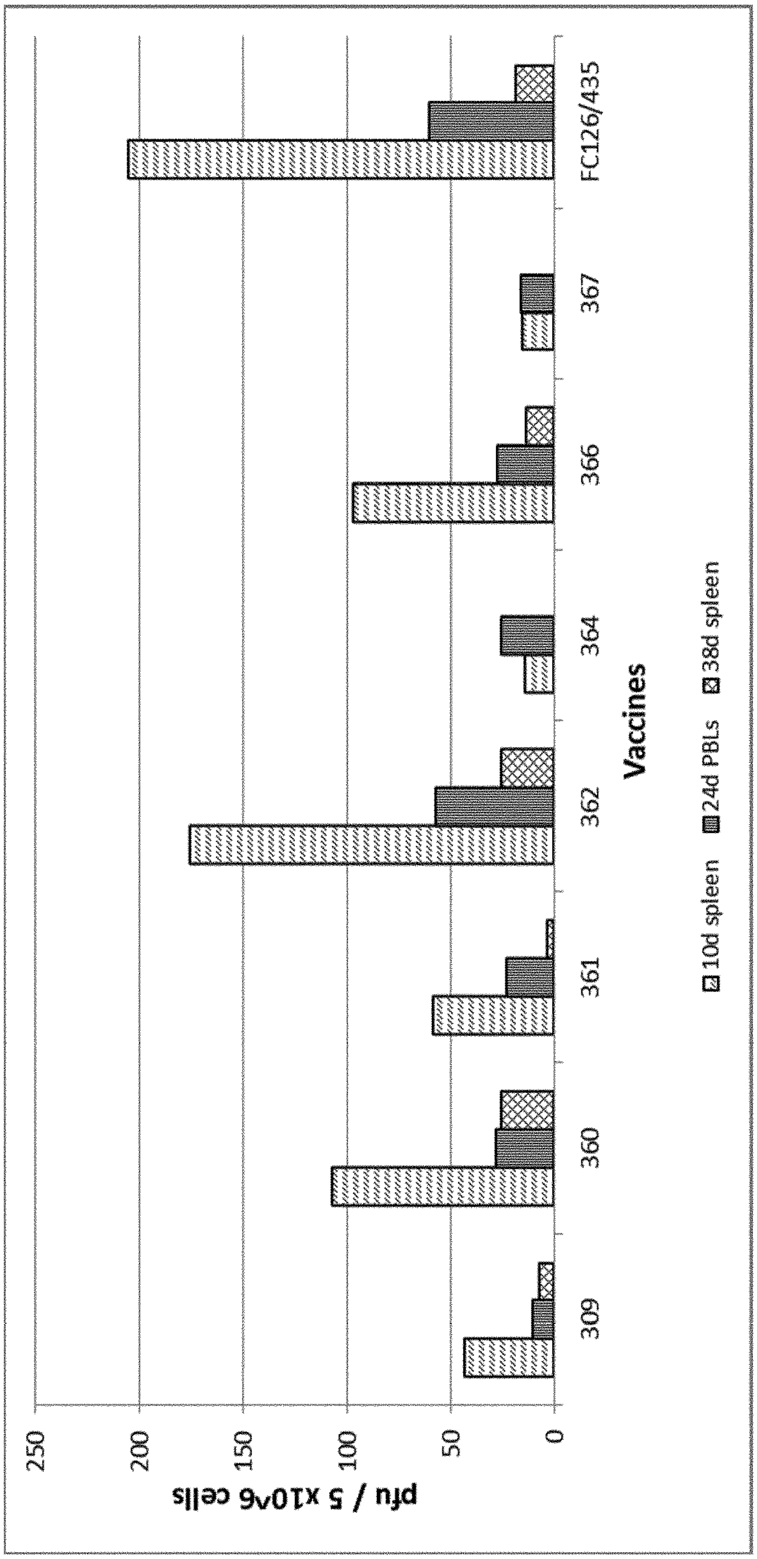

In an animal trial the vireamia and serological responses induced by the various recombinants HVT constructs were tested. Animal experiments were performed essentially as described in WO 2013/057.235. In short: one day-old SPF layer chickens were vaccinated intramuscularly and kept in isolators under negative pressure. At 10, 24 and 38 days post vaccination, HVT virus was re-isolated from spleen (10 and 38 days) or from blood samples (24 days; peripheral blood lymphocytes: PBL), to test vireamia. Serological responses were determined in blood samples taken at 37 days post vaccination. Results are presented in Table 2 and in FIGS. 3 and 4.

TABLE 2

Vireamia and serological responses of different recombinant HVT constructs, tested in SPF layers vaccinated im at 1 day-old

| | | dose | Vireamia (1) | | | serology at 37 d.p.v. (2 Log) | |
|---|---|---|---|---|---|---|---|
| Vaccine | Expression cassette | (pfu) | 10 d | 24 d | 38 d | HI-NDV | VN-IBDV |
| HVP309 | hIE-NDV/F + ß.act.-IBDV/VP2 | 2760 | 43 | 10 | 7 | 2.9 | 8.2 |
| HVP360 | mIE-IBDV/VP2 + hIE-NDV/F | 2320 | 107 | 28 | 25 | 3.4 | 10 |
| HVP361 | LTR-IBDV/VP2 + hIE-NDV/F | 2320 | 58 | 23 | 3 | 3.8 | 0.7 |
| HVP362 | gB-IBDV/VP2* + hIE-NDV/F | 3060 | 175 | 57 | 25 | 3.4 | <0.5 |
| HVP364 | LTR-IBDV/VP2* + hIE-NDV/F | 3480 | 14 | 25 | | 3.1 | 4.8 |
| HVP366 | hIE-NDV/F + gB-IBDV/VP2* | 3340 | 97 | 27 | 13 | 5 | <0.5 |
| HVP367 | hIE-NDV/F + LTR-IBDV/VP2* | 2300 | 15 | 16 | | 2.4 | 4.4 |
| FC-126/435 | Parental HVT (from cosmids) | 2600 | 205 | 60 | 18 | 0.8 | <0.5 |

VP2* = IBDV VP2 gene - codon optimised for HVT
(1) Vireamia is expressed in pfu/5x10^6 spleen cells All HVT recombinants replicated in the vaccinated chickens. Vireamia levels of HVP364 and its mirrored construct HVP367 were low compared to the other recombinants. A portion of the plaques of both viruses from vireamia at 10 and 24 days, showed no expression of VP2 and/or F in IF-assays. Vireamia levels at 38 days were therefore not performed, and HVP364 and HVP367 were excluded from further studies. All other recombinants showed expression of VP2 and F in all plaques at all-time points tested.

Figure 4:
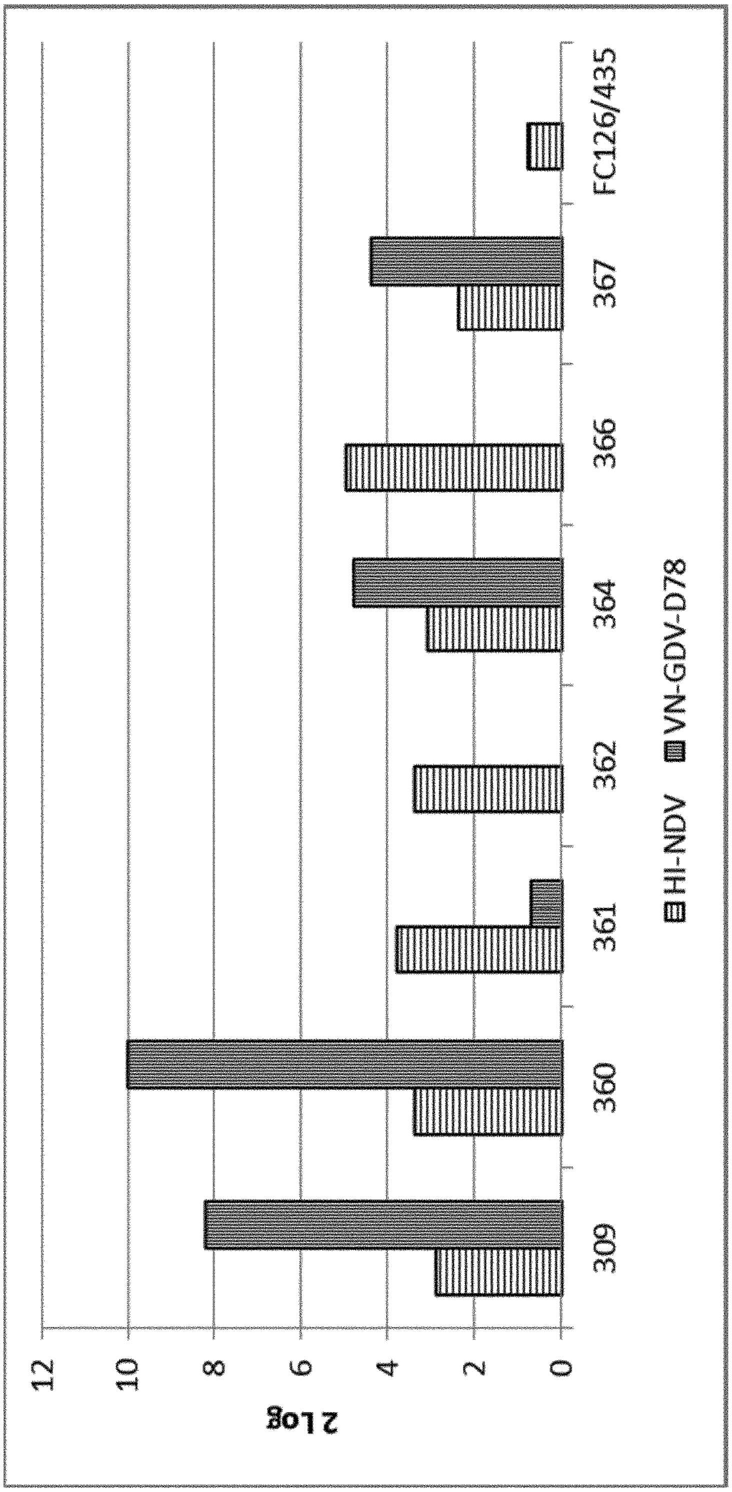

The serological responses induced upon inoculation in experimental animals were determined: for NDV F Elisa values were not discriminatory, therefore heamagglutination (HI) against NDV (Clone 30) was used as a selection tool; for IBDV neutralisation (VN) against D78 was used; FIG. 4.

Even though HVP364 and HVP367 showed non-expressing plaques, antibody induction was measured. The recombinant HVT HVP362 gave excellent vireamia, but no serum response against IBDV VP2. Similarly, HVP361 and HVP366 did give seroconversion against NDV, but very little or none at all against IBDV. Consequently, these three recombinants were also excluded from further studies. Surprisingly, only the HVP360 construct gave good vireamia and serology levels, and this recombinant HVT was therefore selected for further studies.

3. Characterisation of Recombinant HVT: HVP360

3.1. Introduction

HVP360 is a recombinant HVT according to the invention, and expresses both the IBDV VP2 gene and the NDV F gene. An HVT FC-126 based cosmid set was used to insert its expression cassette in the Us2 gene locus on the HVT genome.

In HVP360, the VP2 gene of IBDV was isolated from the classic type F52/70 strain and is driven by the IE1 gene promoter from mCMV strain ATCC VR-194. The F gene originated from NDV vaccine strain Clone 30 and is driven by the IE1 gene promoter from hCMV strain AD169. Also HVP360 contains the SV40 termination signal and the hCMV IE1 gene terminator, as defined herein. FIG. 1 shows a schematic view of the expression cassette in HVP360, with all elements drawn to scale, and flanking sequences of the HVT Us2 gene. In this example, the construction and characterization of HVP360 is described

3.2. Materials and Methods

3.2.1. Construction of HVP Recombinants

For the construction of HVP360, insertion of the recombinant DNA expression cassette into the HVT Us2 gene locus was performed with a set of overlapping cosmid-derived DNA fragments from HVT vaccine strain FC-126 that, after transfection into CEF, regenerated infectious virus, as described in WO 2013/057.235. Also a pBR322 based plasmid was used as transfer vector. Where possible unique restriction enzyme digestion sites were used; when not available these were introduced by PCR directed insertion of a synthetic linker sequence that comprised such a unique site.

The viral DNA fragments from the cosmid vectors and from the transfer plasmid were excised by digestion with appropriate restriction enzymes. The linear DNA fragments were then transfected into CEF cells by means of calcium phosphate precipitation. After DNA had entered the cell, infectious HVT virus was regenerated by homologous recombination between the overlapping sequences of the DNA fragments, thereby generating an intact HVT FC-126 genome, comprising the expression cassette in Us2. This virus construct was called HVP360.

Progeny of the transfected cultures was amplified once on fresh CEF and checked for the presence of HVT expressing VP2 and F by immunofluorescence assay (IFA) using monoclonal antisera against these antigens. Recombinant virus was isolated by single-plaque purification: monolayers of infected CEF were covered with agarose in culture medium, when HVT CPE was clearly visible. Several plaques were picked randomly and passaged two times on CEF before harvesting and storage as cell associated virus preparation.

Two HVP360 parallel plaque isolates (A1 and B1) were each passaged fifteen times in consecutive CEF cell cultures, and screened for expression of VP2 and F by IFA at different passage levels.

3.2.2. DNA Analyses

For detailed characterisation of the HVP360 construct, several DNA analyses were performed on plasmid DNA of the transfer vector, and on total DNA of CEF cultures infected with FC-126 or with HVP360 passage 5 from both parallel isolates. Sequence analysis and Southern blot analysis of the coding nucleotide sequence of the inserted cassette and HVT Us2 flanking regions were performed to confirm correct integration into Us2, and genetic stability upon passaging. Southern blot analysis was also performed on the full genome of HVP360 to confirm correct recombination at the overlapping regions of the HVT DNA fragments from the cosmid set that were used to reconstruct the virus.

HVT DNA was isolated from CEF cell cultures infected with HVP360 or control parental HVT FC-126 that had also been assembled from a set of cosmids as used for HVP360 but without Us2 expression cassette; this was used as control virus in subsequent experiments, and called HVT FC-126/435. Virus stocks were passaged once on CEF and total DNA was isolated using the Easy-DNA™ kit (Invitrogen). Plasmid DNA of the transfervector was isolated from *E. coli* cultures transformed with the transfer vector, and DNA was isolated using the Quantum Prep™ Plasmid Midiprep kit (Bio-Rad).

3.2.3. Characterisation by Southern Blot

Southern blots were performed for an in depth analysis of the genome structure of HVP360 to verify that virus assemblage was exactly as intended and no unintended insertions or deletions had occurred during the virus regeneration.

HVT viral DNA was digested with restriction enzymes PvuI and AatII; or with BamHI, KpnI, Bg/II and EcoRI. Transfer plasmid DNA was digested with restriction enzymes PvuI and AatII.

After digestion DNA fragments were loaded in multiple parallel lanes on 0.7% agarose/TAE gels, electrophoresed, and transferred onto a nitrocellulose membrane. Blots were cut in identical pieces and hybridized individually with one of the $^{32}P$ labelled HVT probes and a probe that detects the DNA size marker (Smartladder™, Eurogentec). After 16 h incubation, excess probe was removed in two wash steps and the blot exposed to an X-ray film. After developing the autoradiogram, DNA restriction fragments specifically hybridizing with the probe were visible.

To detect if any parts of the cloning plasmids had been incorporated in the recombinant HVT, a probe was made by digestion of the plasmid pBR322 into smaller fragments with HaeIII. These fragments were labelled with $^{32}P$. All cloning vectors used in HVT reconstruction are derivatives of pBR322, and will be detected by this probe if vector sequences are present. Also, the HVP360 transfer plasmid was used in one lane of the Southern blots as positive control for the detection of plasmid sequences.

To check for correct assembly at the overlapping regions of the cosmid inserts and the repeat regions of the HVT genome, primer pairs were designed to hybridise in these relevant regions and probes were obtained by PCR on HVT FC-126 viral DNA prepared from infected CEF cell cultures. Amplicons were digested into smaller fragments with Sau3AI, labelled with $^{32}P$ and used as probes in the Southern blot hybridization.

Next the various probes were hybridised to HVP360 DNA that had been digested with BamHI, KpnI, BglII or EcoRI.

The restriction fragment lengths detected in the Southern blots, were compared to those expected as based on the published sequence for HVT strain FC-126 (GenBank acc. nr. AF291866).

3.2.4. Characterisation by Sequence Analysis

To confirm correct insertion and stability of the coding sequences, a complete DNA sequence analysis was done on the expression cassette and on the HVT Us2 flanking regions.

To allow the DNA sequencing, specific DNA fragments of the HVT's were amplified by PCR using specific primers. Amplicons were purified using the Qiaquick™ kit (Qiagen). Next, PCR sequencing was performed on these amplicons, using the Big Dye Terminator™ v.3.1 Cycle Sequencing kit (Applied Biosystems), according to the manufacturer's instructions. Sequencing was done using a 3500 series Genetic Analyzer™ (Applied Biosystems). Sequence readings were analysed using Sequencher™ v. 5.0 software (Gene Codes Corporation).

A contiguous sequence was assembled from overlapping sequence readings. Any ambiguities were resolved by repeating sequencing reactions and compiling multiple sequence readings.

3.2.5. Characterisation of Expression by IFA

After transfection, plaque purification and serial passaging, isolates for both parallel isolates of HVP360, from passage levels 5, 10 and 15 were monitored for the maintained expression of the inserted genes by IFA. CEF monolayers were infected with the recombinant isolates, incubated for 2-3 days until CPE was clearly visible, and then fixated with 80% ethanol. Expression of IBDV VP2 or NDV F was detected with monoclonal antibodies as first reagent, and a fluorescein isothiocyanate (FITC) labelled conjugate as secondary antibody, and read by UV microscopy.

3.3. Results 3.3.1. Results of Southern Blot Hybridizations

Genetic homogeneity and -stability was confirmed by Southern blot analysis using specific probes. Blots hybridized with a plasmid pBR322 probe on lanes containing restricted DNA from strain HVP360 and FC-126, gave no signal with the plasmid probe. However the plasmid probe did react positively with lanes containing restricted DNA from the transfer plasmid, showing fragments specific for the plasmid backbone as predicted. Also, plasmid probe was positive for most bands of the DNA size marker.

The same blot was then hybridized with a probe specific for the Us2 insertion locus, again revealing the restriction fragments as predicted.

As expected, a different—expected—banding pattern was observed for the genome region where the expression cassette has been inserted.

Hybridizations showed that the viral genome of HVP360 was reassembled correctly and matched the pattern observed for the parent HVT cosmid-reconstructed strain FC-126/435.

In the hybridizations with probes that detected overlapping sequences and repeat regions, the patterns for HVP360 and FC-126 were found to be largely identical, although in some regions the pattern found differed slightly from the predicted Southern blot hybridization pattern for the junction between unique long and terminal repeat region, based on published DNA sequence for HVT FC-126. However the pattern in these regions is identical for both recombinant—and paternal virus strains.

Consequently, these differences were caused by differences in the sequence of the viral genome of the parental strain HVT FC-126 and the published sequence, and not by rearrangements during assemblage of the virus genome by the cosmid reconstruction technology.

3.3.2. Results of Characterisation by Sequence Analysis

The entire DNA sequence of inserted cassette and flanking regions of the transfer plasmid used was determined by PCR-sequencing. The consensus sequence of the insert in the viral genome of HVP360 was aligned for both isolates A1 and B1, and compared with the sequence in the transfer plasmid, as well as with the sequence of the insertion region of parent strain FC-126. The result of the alignment confirms that the sequence inserted in HVP360 is identical for isolates A1 and B1.

In addition, this sequence was shown to be identical to the original expression cassette in the transfer plasmid. Also, flanking regions of the Us2 insertion locus of the transfer plasmid, of HVP360 A1 and B1, and of FC-126 were all shown to be identical in DNA sequence.

3.3.3. Results of Characterisation of Expression by IFA

Plaque purified virus of HVP360 for both parallel isolates, and from all three passage levels 5, 10 and 15, was screened by IFA, for expression of VP2 and F. All plaques tested showed full expression of the F and VP2 genes. This confirmed functional and stable expression of VP2 and F, up to (at least) cell passage level 15.

3.4. Conclusions

HVP360 is a recombinant HVT expressing both IBDV VP2 and NDV F. Detailed characterization by IFA, Southern blot analysis on viral DNA, and DNA sequencing of the insert and flanking regions, confirmed that two independent HVP360 isolates A1 and B1 both had correctly integrated the expression cassette in the Us2 region of HVT FC-126 and functionally express IBDV VP2 and NDV F genes in infected cultures of CEF during 15 subsequent passages in CEF cells after plaque purification.

The expression cassette and total genome of HVP360 isolates A1 and B1 are correct in that no deletions, rearrangements, or additional foreign sequences were detected in restriction digestion patterns obtained after Southern blot hybridization with a series of HVT specific genomic probes. Only one copy of the insert is integrated in the Us2 region.

After detailed sequence analysis of the expression cassettes and the flanking regions of the Us2 insertion locus, it was concluded that HVP360 A1 and B1 are identical, to each other, to the sequence in the transfer vector, and to the parent virus FC-126.

4. Vaccination-Challenge Trial with HVP360

A vaccination-challenge experiment was performed with recombinant HVT HVP360. In short: one day-old SPF layers were vaccinated intramuscularly with either of the parallel isolates HVP360 A1 or B1. At 3 or at 4 weeks post vaccination, the induced protection was measured against a severe challenge infection with either IBDV or NDV: for IBDV challenge strain CS89 was inoculated at 3000 CID50 in 0.1 ml, by ocular route to each eye; for NDV strain Herts 33/56 was given at 6 Log 10 ELD50 in 0.2 ml per animal, by im route. The level of vireamia of the vaccine and of the control virus was determined by virus reisolation from spleens from inoculated animals. Results are presented in Table 3.

The level of challenge protection was determined as follows:

For NDV challenge the ratio of live-vs-dead animals was determined at 2 weeks after the challenge at 3 or 4 weeks p.v. For example: 18 survivors out of 20 animals in the group gives an NDV protection score of 90%.

For IBDV challenge, the clinical symptoms of the bursa at necropsy 10 days after challenge are given a score between 0 and 5, representing none up to severe lymphocyte depletion. Animals with a score of 0-2 are considered protected, while a score of 3-5 is not protected. The IBD protection is the percentage of animals that was protected (bursa clinical score 0-2) from the number of animals in the group.

The results showed that in this experiment, im vaccination with HVP360 protected chickens of one day-old against ND at 3 weeks after vaccination, for 59 to 73%. At 4 weeks ND protection was 79 to 93%. Protection against IBD at 3 to 4 weeks after vaccination was 93 to 100%.

TABLE 3

Vireamia, serology, and challenge protection against IBDV and NDV, in SPF layers vaccinated im at 1 day-old with HVP360.

| Vaccine | dose (pfu) | Avg. vireamia (1) 10 d | 25 d | HI-NDV (2 Log) 25 d | VN-IBDV (2 Log) 25 d | NDV protection (%) 21 d | 28 d | IBDV protection (%) 21 d | 28 d |
|---|---|---|---|---|---|---|---|---|---|
| 360 A1 | 1880 | 176 | 17 | 3.1 | 6 | 73 | 79 | 94 | 100 |
| 360 B1 | 1820 | 158 | 13 | 3.4 | 6.6 | 59 | 93 | 94 | 93 |
| FC-126/435 | 2440 | 404 | 36 | 0.9 | 0 | 0 | 0 | 0 | 0 |

(1) Vireamia is expressed in pfu/5 × 10^6 spleen cells

5. Onset—and Duration of Immunity Against ND and Against IBD

In a subsequent vaccination-challenge experiment, using HVP360 as vaccine, and challenging with NDV or with IBDV, the onset of immunity and the duration of immunity were determined. HVP360 vaccine virus was at passage level 13; animals were SPF layers, 1 day old; vaccination route was: subcutaneous; vaccination dose was between 1500 and 2500 pfu/animal dose of 0.2 ml. Challenge virus was either IBDV CS89 or NDV Herts 33/56. Control animals were inoculated sc with HVT FC-126/435.

TABLE 4

Protection by HVP360 against challenge infection with NDV or IBDV, in 1 day old chicks by subcutaneous inoculation with a dose of about 1500-2500 pfu/animal.

| | % protection against ND at | | | | |
|---|---|---|---|---|---|
| Vaccine | 2 w | 3 w | 4 w | 6 w | 8 w |
| HVP360 | 20 | 68 | 90 | 100 | 100 |
| HVT FC-126/435 | 0 | 0 | 0 | 0 | 0 |
| | % protection against IBD at | | | | |
| Vaccine | 2 w | 3 w | 4 w | 6 w | 8 w |
| HVP360 | 90 | 95 | 100 | 100 | 100 |
| HVT FC-126/435 | 0 | 5 | 0 | 0 | 0 |

The results showed that after vaccination with HVP360, more than 90% protection is obtained against challenge with NDV at 4 weeks after vaccination at day old by sc route. This meets the PhEur 0450 monograph requirements for a live ND vaccine.

Even better was the protection achieved against challenge with IBDV: more than 90% protection is obtained against challenge at 2 weeks after vaccination with HVP360. This meets the PhEur 0587 monograph requirements for an IBD vaccine.

Also these results demonstrate that the duration of immuno-protection proceeds until (at least) 8 weeks post vaccination at a level of 100% protection against ND, and against IBD.

6. Testing of Dose-Response Against ND, and Different Routes of Administration In an animal trial, vaccination with different doses of HVP360 was applied, and different routes were tested: in ovo (io) and subcutaneous (sc), to test the response from these doses and these routes against challenge infection with NDV. In addition the vireamia levels of HVP360 vaccine and of FC-126 control virus upon reisolation from inoculated animals in the various treatment groups were determined.

After vaccination of 18 day-old embryonated eggs of SPF layers (io), or one day-old SPF layers by sc route, animals were challenged at 3 or at 4 weeks old with NDV Herts 33/56. Vaccine/control virus was re-isolated from spleens or blood samples at 4, 11 or 17 days to determine the vireamia levels reached. Results are presented in Table 5. Vireamia is represented in two ways: once as number of birds positive for vaccine/control virus re-isolation out of the total number of birds in that group, and once as average virus pfu per 2×10^6 spleen cells.

In the column 'dose' the actual inoculation dose is presented, determined by back-titration of rests of the inocula after the vaccination.

TABLE 5

Vireamia and challenge protection against NDV in SPF layers vaccinated in ovo or subcutaneous with different doses of HVP360

| | dose | Pos/total - avg. vireamia (pfu/2 × 10^6 cells) | | | NDV protection (%) | |
|---|---|---|---|---|---|---|
| Vaccine | (pfu) | 4d. | 11d. | 17d. | 3 wk. | 4 wk. |
| HVP360 | 600 | | 8/8 - 117 | | 65 | 89 |
| | 1563 | | 9/10 - 112 | | 70 | 85 |
| FC-126 | 975 | | 10/10 - 136 | | 0 | 0 |
| | 2475 | | 9/10 - 116 | | 0 | 0 |
| HVP360 | 2456 | 10/10 - 54 | | 5/5 - 83 | 65 | 84 |
| FC-126 | 2481 | 10/10 - 143 | | 4/5 - 171 | 0 | 0 |

Subcutaneous vaccination appeared to be little dependant on the dose used; doses between 500 and 2500 pfu/animal all reached satisfactory immunoprotection levels.

Ultimately, both routes (io and sc) could raise the same protection at 3 and 4 weeks, of 65-70% and 84-90% respectively.

LEGEND TO THE FIGURES

FIG. 1

Schematic view of the insert section of a preferred recombinant DNA molecule according to the invention, comprising the expression cassette and Us2 gene flanking sequences, that was used to generate HVP360, a preferred recombinant HVT according to the invention. The elements of the expression cassette are drawn to scale.

Abbreviations (from left to right): 5' US2: flanking upstream sequences from the HVT Us2 gene; mIE: murine CMV IE1 gene promoter; VP2: IBDV VP2 gene; term: SV40 transcription terminator; hIE: human CMV IE1 gene core promoter; F: NDV F gene; term: hCMV IE1 gene terminator; 3' US2: flanking downstream sequences from the HVT Us2 gene.

FIG. 2:

Graphic representation (not drawn to scale), of the relevant elements of a representative number of recombinant HVT constructs tested. For comparison the prior art construct HVP309 is also represented.

FIG. 3:

Vireamia levels of different HVT recombinants at 10, 24 and 38 days post vaccination of one day-old SPF layers, as average per group.

FIG. 4:

Serological responses induced by the different HVT recombinants, at 37 days post vaccination of one day-old SPF layers, as average per group.

The invention claimed is:

1. A recombinant DNA expression cassette comprising in the 5' to 3' direction and in the following order:

a. a murine cytomegalovirus immediate early 1 gene (mCMV-IE1) promoter, b. an infectious bursal disease virus (IBDV) viral protein 2 (VP2) gene, c. a transcription terminator, d. a human cytomegalovirus immediate early 1 gene (hCMV-IE1) promoter, and e. a Newcastle disease virus (NDV) fusion (F) protein gene.

2. The recombinant DNA expression cassette of claim 1, wherein one or more or all of the conditions apply selected from the group consisting of: the mCMV-IE1 gene promoter is a complete promoter; the IBDV VP2 gene encodes a VP2 protein from a classic type IBDV; the transcription terminator comprises both a terminator region and a polyA region; the transcription terminator is derived from simian virus 40 (SV40); the hCMV-IE1 gene promoter is a core promoter; the NDV F gene is from a lentogenic NDV strain; the expression cassette comprises an additional transcription terminator which is located downstream of the NDV F gene; and the additional transcription terminator is derived from the hCMV-IE1 gene.

3. A recombinant DNA molecule comprising the recombinant DNA expression cassette of claim 1.

4. A recombinant herpes virus of turkeys virus (HVT), comprising the recombinant DNA expression cassette of claim 1, wherein the expression cassette is inserted in the Us region of the genome of the recombinant HVT.

5. A host cell comprising the recombinant HVT of claim 4.

6. A vaccine for poultry comprising the recombinant HVT of claim 4, and a pharmaceutically acceptable carrier.

7. The vaccine of claim 6, comprising at least one additional immunoactive component.

8. A vaccine for poultry comprising the host cell of claim 5 and a pharmaceutically acceptable carrier.

9. The vaccine of claim 8, comprising at least one additional immunoactive component.

10. A recombinant herpes virus of turkeys virus (HVT), comprising the recombinant DNA expression cassette of claim 2, wherein the expression cassette is inserted in the Us region of the genome of the recombinant HVT.

11. A host cell comprising the recombinant HVT of claim 10.

12. A vaccine for poultry comprising the host cell of claim 11 and a pharmaceutically acceptable carrier.

13. A method of constructing the recombinant HVT of claim 4, said method comprising the insertion of the recombinant DNA expression cassette into the Us region of the genome of the recombinant HVT.

14. A method of preparing the vaccine of claim 6, said method comprising the steps of:

infecting host cells with the recombinant HVT, harvesting the infected host cells, and admixing the harvested infected host cells with a pharmaceutically acceptable carrier.

15. A method for preventing or reducing infection by IBDV, NDV, or IBDV and NDV, or associated signs of disease, the method comprising the administration of the vaccine of claim 6 to poultry.

16. A method of vaccinating poultry, comprising the step of inoculating poultry with the vaccine of claim 6.

17. A method of vaccinating poultry, comprising the step of inoculating poultry with the vaccine of claim 7.

18. A method for preventing or reducing infection by IBDV, NDV, or IBDV and NDV, or associated signs of disease in poultry, the method comprising the administration of the vaccine of claim 7 to poultry.

* * * * *